United States Patent
Yonemura et al.

(10) Patent No.: US 11,220,529 B2
(45) Date of Patent: Jan. 11, 2022

(54) RECOMBINANT BAGWORM SILK

(71) Applicant: National Agriculture and Food Research Organization, Ibaraki (JP)

(72) Inventors: Naoyuki Yonemura, Ibaraki (JP); Tetsuya Iizuka, Ibaraki (JP); Kenichi Nakajima, Ibaraki (JP); Takuya Tsubota, Ibaraki (JP); Takao Suzuki, Ibaraki (JP); Hideki Sezutsu, Ibaraki (JP); Tsunenori Kameda, Ibaraki (JP); Taiyo Yoshioka, Ibaraki (JP)

(73) Assignee: NATIONAL AGRICULTURE AND FOOD RESEARCH ORGANIZATION, Ibaraki (JP)

(*) Notice: Subject to any disclaimer, the term of this patent is extended or adjusted under 35 U.S.C. 154(b) by 0 days.

(21) Appl. No.: 16/342,837

(22) PCT Filed: Oct. 16, 2017

(86) PCT No.: PCT/JP2017/037327
§ 371 (c)(1),
(2) Date: Apr. 17, 2019

(87) PCT Pub. No.: WO2018/074403
PCT Pub. Date: Apr. 26, 2018

(65) Prior Publication Data
US 2019/0256565 A1    Aug. 22, 2019

(30) Foreign Application Priority Data

Oct. 18, 2016 (JP) .............................. JP2016-204592

(51) Int. Cl.
| | | |
|---|---|---|
| A01K 67/033 | (2006.01) | |
| C07K 14/435 | (2006.01) | |
| C12N 15/85 | (2006.01) | |
| A01K 67/04 | (2006.01) | |
| C12N 15/09 | (2006.01) | |
| D01B 7/06 | (2006.01) | |
| D01B 7/00 | (2006.01) | |

(52) U.S. Cl.
CPC .... *C07K 14/43563* (2013.01); *A01K 67/0333* (2013.01); *A01K 67/04* (2013.01); *C12N 15/09* (2013.01); *C12N 15/8509* (2013.01); *A01K 2217/206* (2013.01); *A01K 2227/70* (2013.01); *C07K 14/435* (2013.01); *C12N 2830/008* (2013.01); *D01B 7/00* (2013.01); *D01B 7/06* (2013.01)

(58) Field of Classification Search
CPC .................................................. A01K 67/0333
See application file for complete search history.

(56) References Cited

FOREIGN PATENT DOCUMENTS

| WO | 2012050919 A2 | 4/2012 | |
|---|---|---|---|
| WO | WO-2015042164 A2 * | 3/2015 | ............... D01D 5/00 |

OTHER PUBLICATIONS

Zhou et al. (2000, Nucleic Acid Res., vol. 28(12), pp. 2413-2419) (Year: 2000).*
Zhou et al. (2000, Nucleic Acids Res., vol. 28(12), pp. 2413-2419) (Year: 2000).*
Asakura et al. (2003, Biomacromolecules, vol. 4, pp. 815-820) (Year: 2003).*
Reddy et al. (2010, J. Mater. Sci., vol. 45, pp. 6617-6622) (Year: 2010).*
Imamura et al. (2003, Genetics, vol. 165, pp. 1329-1340) (Year: 2003).*
Sehnal et al., 2004, Biomacromolecules, vol. 5, pp. 666-674 (Year: 2004).*
Fu et al. (2009, Chem. Commun., pp. 6515-6529) (Year: 2009).*
Tsubota et al. (2020, Insect Sci., vol. 0, pp. 1-16) (Year: 2020).*
Sequence for Seq Id No. 2246 from Kittleson—1 page printout (Year: 2015).*
Fu et al., "Animal silks: their structures, properties and artificial production",Chem. Commun., Jan. 1, 2009, No. 43, pp. 6515-6529.
Reddy et al., "Structure and properties of ultrafine silk fibers produced by Theriodopteryx ephemeraeformis", J Mater Sci 2010, vol. 45, No. 24, pp. 6617-6622.
Supplementary European Search Report for Corresponding European Application No. 17862918.4 dated (Feb. 19, 2020) (11 Pages).
Zhou, Cong-Zhao et al., "Fine organization of Bombyx mori fibroin heavy chain gene", Nucleic Acids Research, 2000, vol. 28, No. 12, pp. 2413-2419.
"Bombyx mori fibroin heavy chain Fib-H (fib-H) gene, complete cds". Accession No. AF226688, Genbank[online], 2000, pp. 1-20.
Office Action for Japanese Patent Application No. 2018-546315, dated Jul. 20, 2021, pp. 1-4.

* cited by examiner

*Primary Examiner* — Thaian N. Ton
*Assistant Examiner* — David A Montanari
(74) *Attorney, Agent, or Firm* — Lucas & Mercanti, LLP

(57) ABSTRACT

A method of producing a transgenic silkworm that spins bagworm silks and producing a large quantity of bagworm silks by transgenic technology is developed and provided. A gene encoding a modified bagworm Fib H and a transgenic silkworm in which the gene is introduced, wherein the gene is obtained by cloning a gene fragment encoding a bagworm Fib H-like polypeptide comprising a partial amino acid sequence of bagworm Fib H, and fusing the gene fragment to a gene fragment encoding silkworm-derived Fib H, are provided.

10 Claims, 2 Drawing Sheets
Specification includes a Sequence Listing.

A  B

SEQUENCE LISTING

<160> NUMBER OF SEQ ID NOS: 33

<210> SEQ ID NO 1
<211> LENGTH: 13
<212> TYPE: PRT
<213> ORGANISM: Eumeta japonica

<400> SEQUENCE: 1

Gly Ala Gly Ala Gly Ala Gly Ser Gly Ala Gly Ala Gly
1               5                   10

<210> SEQ ID NO 2
<211> LENGTH: 39
<212> TYPE: DNA
<213> ORGANISM: Eumeta japonica

<400> SEQUENCE: 2
ggagccggag caggtgccgg ttcaggcgcc ggtgctgga                                39

<210> SEQ ID NO 3
<211> LENGTH: 39
<212> TYPE: DNA
<213> ORGANISM: Eumeta japonica

<400> SEQUENCE: 3
ggtgccggag caggagctgg atcaggtgca ggagcaggt                                39

<210> SEQ ID NO 4
<211> LENGTH: 39
<212> TYPE: DNA
<213> ORGANISM: Eumeta japonica

<400> SEQUENCE: 4
ggtgcgggcg ctggagcagg ttccggagca ggagcaggt                                39

<210> SEQ ID NO 5
<211> LENGTH: 140
<212> TYPE: PRT
<213> ORGANISM: Eumeta japonica

<400> SEQUENCE: 5

Val Val Tyr Val Ser Ala Gly Gly Ala Gly Ala Gly Ala Gly Ser Gly
1               5                   10                  15

Ala Gly Ala Gly Ser Gly Ala Gly Ala Gly Ala Gly Ser Gly Ala Gly
            20                  25                  30

Ala Gly Gly Ala Gly Ala Ala Ala Gly Ala Gly Ala Gly Ala Gly Ser
        35                  40                  45

Gly Ala Gly Ser Gly Ser Gly Ala Gly Ala Gly Ala Gly Ser Gly Ala
    50                  55                  60

Gly Ala Gly Ser Gly Ala Gly Ala Gly Ala Gly Ser Gly Ala
65                  70                  75                  80

Ala Gly Gly Ala Gly Ala Gly Ala Gly Ala Gly Ala Ala Ala Ala
                85                  90                  95

Ala Ala Ala Ala Glu Ala Ala Ala Ala Ala Ala Ala Ala
            100                 105                 110

Ala Gly Ser Gly Ala Gly Ala Gly Gly Ala Gly Gly Tyr Gly Ala Gly
            115                 120                 125

Ala Gly Ala Gly Ala Gly Ala Gly Ala Gly Gly Ala
        130                 135                 140

<210> SEQ ID NO 6
<211> LENGTH: 420
<212> TYPE: DNA
<213> ORGANISM: Eumeta japonica

<400> SEQUENCE: 6

```
gtcgtctacg taagtgctgg aggagccgga gcaggtgccg gttcaggcgc cggtgctgga      60
tcgggtgccg gagcaggagc tggatcaggt gcaggagcag gtggagcagg agccgcagcc     120
ggagctggtg ctggtgctgg ttcaggtgca ggatccggtt caggtgcggg cgctggagca     180
ggttccggag caggagcagg ttccggtgct ggtgcaggag caggagctgg ttcaggtgca     240
gcaggtggag caggagctgg cgctggcgct ggcgctgcag ccgcagccgc agcagcagca     300
gaagcggcag ccgcagctgc cgccgccgct gccgccgcag gtagtggagc aggcgctgga     360
ggagccggag gctacggagc gggagctgga gcaggtgccg gtgcaggtgc tggcggcgca     420
```

<210> SEQ ID NO 7
<211> LENGTH: 308
<212> TYPE: PRT
<213> ORGANISM: Eumeta japonica

<400> SEQUENCE: 7

Ile Ala Ala Ser Val Gly Ala Gly Val Gly Ala Ala Ser Val Ala Gly
1               5                   10                  15

Ala Gly Thr Gly Ala Gly Ser Gly Ala Ala Gly Ala Gly Ala
        20                  25                  30

Ala Asp Ala Gly Ala Ala Ala Ala Ala Ala Ala Gln Ala Ala
            35                  40                  45

Ala Ala Asp Ala Ala Ala Ala Gly Ser Gly Ala Gly Ala Gly Arg Val
    50                  55                  60

Gly Ala Tyr Gly Pro Tyr Gly Gly Leu Ala Ser Ala Gly Ala Gly Gly
65                  70                  75                  80

Ala Gly Gly Ala Gly Gly Ala Gly Gly Tyr Ser Gly Ala Ser Val Val
                85                  90                  95

Tyr Val Ser Ala Gly Gly Ala Gly Ala Gly Ala Gly Ser Gly Ala Gly
                100                 105                 110

Ala Gly Ser Gly Ala Gly Ala Gly Ala Gly Ser Gly Ala Gly Ala Gly
            115                 120                 125

Gly Ala Gly Ala Ala Ala Gly Ala Gly Ala Gly Ser Gly Ala
        130                 135                 140

Gly Ser Gly Ser Gly Ala Gly Ala Gly Ala Gly Ser Gly Ala Gly Ala
145                 150                 155                 160

Gly Ser Gly Ala Gly Ala Gly Ala Gly Ala Gly Ser Gly Ala Ala Gly
                165                 170                 175

Gly Ala Gly Ala Gly Ala Gly Ala Ala Ala Ala Ala Ala
            180                 185                 190

Ala Ala Glu Ala Ala Ala Ala Ala Ala Ala Ala Ala Gly
        195                 200                 205

Ser Gly Ala Gly Ala Gly Gly Ala Gly Tyr Gly Ala Gly Ala Gly
    210                 215                 220

Ala Gly Ala Gly Ala Gly Ala Gly Ala Ser Gly Gly Tyr Gly Ser
225                 230                 235                 240

Tyr Gly Ser Gly Val Ala Ala Gly Ala Gly Gly Ala Gly Val Gly
                245                 250                 255

Gly Ser Arg Gly Ala Gly Val Gly Ala Gly Val Gly Ala Gly Tyr Gly
                260                 265                 270

Ser Ala Leu Asn Ser Gly Ala Gly Ala Gly Ala Gly Ala Gly
        275                 280                 285

Ala Gly Gly Ala Ala Gly Ala Gly Ala Gly Ala Gly Ala Gly
        290                 295                 300

Ala Gly Ala Gly
305

<210> SEQ ID NO 8
<211> LENGTH: 924
<212> TYPE: DNA
<213> ORGANISM: Eumeta japonica

<400> SEQUENCE: 8

| | | | | | |
|---|---|---|---|---|---|
| atagcagcca | gtgtaggtgc | gggcgttgga | gcagcttccg | ttgctggtgc | aggaacagga | 60 |
| gctggctcag | gtgcagctgg | tggagcagga | gcaggtgctg | acgctggcgc | tgcagccgcc | 120 |
| gctgcggcag | cagcacaagc | agcagccgca | gatgctgccg | ccgcaggtag | tggcgctggt | 180 |
| gctggacgag | tcggagctta | cggaccctac | ggaggtttag | caagcgctgg | tgctggtggt | 240 |
| gctggcggag | ccggtggtgc | aggtggatac | agtggtgcaa | gtgtcgtcta | cgtaagtgct | 300 |
| ggaggagccg | agcaggtgc | cggttcaggc | gccggtgctg | gatcgggtgc | cggagcagga | 360 |
| gctggatcag | gtgcaggagc | aggtggagca | ggagccgcag | ccggagctgg | tgctggtgct | 420 |
| ggttcaggtg | caggatccgg | ttcaggtgcg | ggcgctggga | caggttccgg | agcaggagca | 480 |
| ggttccggtg | ctggtgcagg | agcaggagct | ggttcaggtg | cagcaggtgg | agcaggagct | 540 |
| ggcgctggcg | ctggcgctgc | agccgcagcc | gcagcagcag | cagaagcggc | agccgcagct | 600 |
| gctgccgccg | ctgccgccgc | aggtagtgga | gcaggcgctg | gaggagccgg | aggctacgga | 660 |
| gcgggagctg | gagcaggtgc | cggtgcaggt | gctggcggcg | catctggagg | ctacggttct | 720 |
| tacggatcgg | gagttgcagc | aggtgccggt | gcaggagctg | gtgttggtgg | tagcagggga | 780 |
| gcaggtgttg | cgctggtgt | tggtgctggt | tatggctccg | cattgaattc | aggagccggt | 840 |
| gccggagcag | gtgctggtgc | tggagctggt | ggtgctgcag | gagctggtgc | tggtgcagga | 900 |
| gcaggagctg | gcgctggagc | tgga | | | | 924 |

<210> SEQ ID NO 9
<211> LENGTH: 530
<212> TYPE: PRT
<213> ORGANISM: Artificial
<220> FEATURE:
<223> OTHER INFORMATION: chimeric protein

<400> SEQUENCE: 9

Met Arg Val Lys Thr Phe Val Ile Leu Cys Cys Ala Leu Gln Tyr Val
1               5                   10                  15

Ala Tyr Thr Asn Ala Asn Ile Asn Asp Phe Asp Glu Asp Tyr Phe Gly
            20                  25                  30

Ser Asp Val Thr Val Gln Ser Ser Asn Thr Thr Asp Glu Ile Ile Arg
        35                  40                  45

Asp Ala Ser Gly Ala Val Ile Glu Glu Gln Ile Thr Thr Lys Lys Met
    50                  55                  60

Gln Arg Lys Asn Lys Asn His Gly Ile Leu Gly Lys Asn Glu Lys Met
65                  70                  75                  80

Ile Lys Thr Phe Val Ile Thr Thr Asp Ser Asp Gly Asn Glu Ser Ile
                85                  90                  95

Val Glu Glu Asp Val Leu Met Lys Thr Leu Ser Asp Gly Thr Val Ala

```
               100                 105                 110
    Gln Ser Tyr Val Ala Ala Asp Ala Gly Ala Tyr Ser Gln Ser Gly Pro
            115                 120                 125

Tyr Val Ser Asn Ser Gly Tyr Ser Thr His Gln Gly Tyr Thr Ser Asp
            130                 135                 140

Phe Ser Thr Ser Ala Ala Val Gly Ala Gly Ser Ile Ala Ala Ser Val
    145                 150                 155                 160

Gly Ala Gly Val Gly Ala Ala Ser Val Ala Gly Ala Gly Thr Gly Ala
                        165                 170                 175

Gly Ser Gly Ala Ala Gly Gly Ala Gly Ala Gly Asp Ala Gly Ala
                    180                 185                 190

Ala Ala Ala Ala Ala Ala Ala Gln Ala Ala Ala Ala Asp Ala Ala
                195                 200                 205

Ala Ala Gly Ser Gly Ala Gly Ala Gly Arg Val Gly Ala Tyr Gly Pro
                210                 215                 220

Tyr Gly Gly Leu Ala Ser Ala Gly Ala Gly Gly Ala Gly Gly Ala Gly
    225                 230                 235                 240

Gly Ala Gly Gly Tyr Ser Gly Ala Ser Val Val Tyr Val Ser Ala Gly
                        245                 250                 255

Gly Ala Gly Ala Gly Ala Gly Ser Gly Ala Gly Ala Gly Ser Gly Ala
                    260                 265                 270

Gly Ala Gly Ala Gly Ser Gly Ala Gly Ala Gly Ala Gly Ala Ala
                    275                 280                 285

Ala Gly Ala Gly Ala Gly Ala Gly Ser Gly Ala Gly Ser Gly Ser Gly
            290                 295                 300

Ala Gly Ala Gly Ala Gly Ser Gly Ala Gly Ala Gly Ser Gly Ala Gly
    305                 310                 315                 320

Ala Gly Ala Gly Ala Gly Ser Gly Ala Ala Gly Gly Ala Gly Ala Gly
                        325                 330                 335

Ala Gly Ala Gly Ala Ala Ala Ala Ala Ala Ala Ala Glu Ala Ala
                    340                 345                 350

Ala Ala Ala Ala Ala Ala Ala Ala Ala Gly Ser Gly Ala Gly Ala
                    355                 360                 365

Gly Gly Ala Gly Gly Tyr Gly Ala Gly Ala Gly Ala Gly Ala Gly Ala
            370                 375                 380

Gly Ala Gly Gly Ala Ser Gly Gly Tyr Gly Ser Tyr Gly Ser Gly Val
    385                 390                 395                 400

Ala Ala Gly Ala Gly Ala Gly Ala Gly Val Gly Gly Ser Arg Gly Ala
                        405                 410                 415

Gly Val Gly Ala Gly Val Gly Ala Gly Tyr Gly Ser Ala Leu Asn Ser
                    420                 425                 430

Gly Ala Gly Ala Gly Ala Gly Ala Gly Ala Gly Ala Gly Gly Ala Ala
                    435                 440                 445

Gly Ala Gly Ala Gly Ala Gly Ala Gly Ala Gly Ala Gly Ala Gly Val
                    450                 455                 460

Asp Ser Val Ser Tyr Gly Ala Gly Arg Gly Tyr Gly Gln Gly Ala Gly
    465                 470                 475                 480

Ser Ala Ala Ser Ser Val Ser Ser Ala Ser Arg Ser Tyr Asp Tyr
                        485                 490                 495

Ser Arg Arg Asn Val Arg Lys Asn Cys Gly Ile Pro Arg Arg Gln Leu
                    500                 505                 510

Val Val Lys Phe Arg Ala Leu Pro Cys Val Asn Cys His His His
                    515                 520                 525
```

His His
    530

<210> SEQ ID NO 10
<211> LENGTH: 1590
<212> TYPE: DNA
<213> ORGANISM: Artificial
<220> FEATURE:
<223> OTHER INFORMATION: chimeric protein

<400> SEQUENCE: 10

| | | | | | |
|---|---|---|---|---|---|
| atgagagtca | aaacctttgt | gatcttgtgc | tgcgctctgc | agtatgtcgc | ttatacaaat | 60 |
| gcaaacatca | atgattttga | tgaggactat | tttgggagtg | atgtcactgt | ccaaagtagt | 120 |
| aatacaacag | atgaaataat | tagagatgca | tctggggcag | ttatcgaaga | acaaattaca | 180 |
| actaaaaaaa | tgcaacggaa | aaataaaaac | catggaatac | ttggaaaaaa | tgaaaaaatg | 240 |
| atcaagacgt | tcgttataac | cacggattcc | gacggtaacg | agtccattgt | agaggaagat | 300 |
| gtgctcatga | agacactttc | cgatggtact | gttgctcaaa | gttatgttgc | tgctgatgcg | 360 |
| ggagcatatt | ctcagagcgg | gccatacgta | tcaaacagtg | gatacagcac | tcatcaagga | 420 |
| tatacgagcg | atttcagcac | tagtgctgca | gtcggtgcag | gatctatagc | agccagtgta | 480 |
| ggtgcgggcg | ttggagcagc | ttccgttgct | ggtgcaggaa | caggagctgg | ctcaggtgca | 540 |
| gctggtggag | caggagcagg | tgctgacgct | ggcgctgcag | ccgccgctgc | ggcagcagca | 600 |
| caagcagcag | ccgcagatgc | tgccgccgca | ggtagtggcg | ctggtgctgg | acgagtcgga | 660 |
| gcttacggac | cctacggagg | tttagcaagc | gctggtgctg | gtggtgctgg | cggagccggt | 720 |
| ggtgcaggtg | gatacagtgg | tgcaagtgtc | gtctacgtaa | gtgctggagg | agccggagca | 780 |
| ggtgccggtt | caggcgccgg | tgctggatcg | ggtgccggag | caggagctgg | atcaggtgca | 840 |
| ggagcaggtg | gagcaggagc | cgcagccgga | gctggtgctg | gtgctggttc | aggtgcagga | 900 |
| tccggttcag | gtgcgggcgc | tggagcaggt | tccggagcag | gagcaggttc | cggtgctggt | 960 |
| gcaggagcag | gagctggttc | aggtgcagca | ggtggagcag | gagctggcgc | tggcgctggc | 1020 |
| gctgcagccg | cagccgcagc | agcagcagaa | gcggcagccg | cagctgctgc | cgccgctgcc | 1080 |
| gccgcaggta | gtggagcagg | cgctggagga | gccggaggct | acggagcggg | agctggagca | 1140 |
| ggtgccggtg | caggtgctgg | cggcgcatct | ggaggctacg | gttcttacgg | atcgggagtt | 1200 |
| gcagcaggtg | ccggtgcagg | agctggtgtt | ggtggtagca | ggggagcagg | tgttggcgct | 1260 |
| ggtgttggtg | ctggttatgg | ctccgcattg | aattcaggag | ccggtgccgg | agcaggtgct | 1320 |
| ggtgctggag | ctggtggtgc | tgcaggagct | ggtgctggtg | caggagcagg | agctggcgct | 1380 |
| ggagctggag | tcgacagcgt | cagttacgga | gctggcaggg | gatacggaca | aggtgcagga | 1440 |
| agtgcagctt | cctctgtgtc | atctgcttca | tctcgcagtt | acgactattc | tcgtcgtaac | 1500 |
| gtccgcaaaa | actgtggaat | tcctagaaga | caactagttg | ttaaattcag | agcactgcct | 1560 |
| tgtgtgaatt | gccatcacca | ccatcaccac | | | | 1590 |

<210> SEQ ID NO 11
<211> LENGTH: 19
<212> TYPE: PRT
<213> ORGANISM: Bombyx mori
<220> FEATURE:
<223> OTHER INFORMATION: signal peptide of serisin 1

<400> SEQUENCE: 11

Met Arg Phe Val Leu Cys Cys Thr Leu Ile Ala Leu Ala Ala Leu Ser

```
1               5                   10                  15
Val Lys Ala

<210> SEQ ID NO 12
<211> LENGTH: 57
<212> TYPE: DNA
<213> ORGANISM: Bombyx mori
<220> FEATURE:
<223> OTHER INFORMATION: nucleic acid sequence coding signal peptide of
      sericin 1

<400> SEQUENCE: 12
atgcgtttcg ttctgtgctg cactttgatt gcgttggctg cgctcagcgt aaaagct        57

<210> SEQ ID NO 13
<211> LENGTH: 18
<212> TYPE: PRT
<213> ORGANISM: Bombyx mori
<220> FEATURE:
<223> OTHER INFORMATION: signal peptide of sericin 2

<400> SEQUENCE: 13

Met Lys Ile Pro Tyr Val Leu Leu Phe Leu Val Gly Val Ala Val Val
1               5                   10                  15

Asn Ala

<210> SEQ ID NO 14
<211> LENGTH: 54
<212> TYPE: DNA
<213> ORGANISM: Bombyx mori
<220> FEATURE:
<223> OTHER INFORMATION: nucleic acid sequence coding signal peptide of
      sericin 2

<400> SEQUENCE: 14
atgaagatcc catacgtctt gctgttcctt gtgggcgtgg ctgtggtcaa cgca           54

<210> SEQ ID NO 15
<211> LENGTH: 18
<212> TYPE: PRT
<213> ORGANISM: Bombyx mori
<220> FEATURE:
<223> OTHER INFORMATION: signal peptide of sericin 3

<400> SEQUENCE: 15

Met Asn Cys Lys Val Ala Leu Phe Leu Ile Val Ala Ile Val Ala Val
1               5                   10                  15

Gln Ala

<210> SEQ ID NO 16
<211> LENGTH: 54
<212> TYPE: DNA
<213> ORGANISM: Bombyx mori
<220> FEATURE:
<223> OTHER INFORMATION: nucleic acid sequence coding signal peptide of
      sericin 3

<400> SEQUENCE: 16
atgaattgta aagttgctct attcctgata gtggctattg tagccgtcca ggct            54

<210> SEQ ID NO 17
<211> LENGTH: 870
<212> TYPE: DNA
<213> ORGANISM: Bombyx mori
<220> FEATURE:
```

<223> OTHER INFORMATION: fibroin H chain promoter

<400> SEQUENCE: 17

```
acaaaactgc cacacgcatt tttttctcca ctgtaggttg tagttacgcg aaaacaaaat      60
cgttctgtga aaattcaaac aaaaatattt tttcgtaaaa acacttatca atgagtaaag     120
taacaattca tgaataattt catgtaaaaa aaaatactag aaaaggaat ttttcattac     180
gagatgctta aaaatctgtt tcaaggtaga gattttcga tatttcggaa aattttgtaa     240
aactgtaaat ccgtaaaatt ttgctaaaca tatattgtgt tgttttggta agtattgacc     300
caagctatca cctcctgcag tatgtcgtgc taattactgg acacattgta taacagttcc     360
actgtattga caataataaa acctcttcat tgacttgaga atgtctggac agatttggct     420
ttgtattttt gatttacaaa tgttttttg gtgattacc catccaaggc attctccagg     480
atggttgtgg catcacgccg attggcaaac aaaaactaaa atgaaactaa aaagaaacag     540
tttccgctgt cccgttcctc tagtgggaga aagcatgaag taagttcttt aaatattaca     600
aaaaaattga acgatattat aaaattcttt aaaatattaa agtaagaac aataagatca     660
attaaatcat aattaatcac attgttcatg atcacaattt aatttacttc atacgttgta     720
tgttatgtt aaataaaaag attaatttct atgtaattgt atctgtacaa tacaatgtgt     780
agatgtttat tctatcgaaa gtaaatacgt caaaactcga aattttcag tataaaaagg     840
ttcaactttt tcaaatcagc atcagttcgg                                      870
```

<210> SEQ ID NO 18
<211> LENGTH: 1110
<212> TYPE: DNA
<213> ORGANISM: Antheraea pernyi
<220> FEATURE:
<223> OTHER INFORMATION: fibroin H chain promoter

<400> SEQUENCE: 18

```
tccagcgtta ccaatgagag cgcttcaaaa ttctttacaa cttcattaga atacgtcgat      60
ttttctctac ttcatataaa tattctatag atgtgtttgc tataacataa atacttttaa     120
aaaaatgtct caacggttgt gaaaactgtc aaaatctgtt gcgtagttca gaaaaactaa     180
ggaaacatac agaaaattta ttttacaaaa gtacggagat atataaaaat atttcgatta     240
ctttagaatt acaataaaac tatttgacaa tttgattgca aatatagacc atgacaacac     300
cacatctttg ttatctaaaa cacgtagcga caacactcct tgaacgttgt tcgaggatta     360
ctacgataat tggcggtttt ttttccgcac cgcaagaaaa gagtagaaat gtaccgtatt     420
taaatccagt gcggaaattt tcacgcagaa tgcgtttcca tacaattcta taggttacat     480
atcttgcgga aataaattcg tgccaaaaag ccgaagtgcg gggactaata aagattttat     540
ttggcattcc ttctaacctt tagatataaa tttctgtacg cgcgtatgtc actgaactcc     600
ccctaaacgg ctggactaat tttgatgaaa tattgtttgt gtgttctagt ggatccgaga     660
attgtttaaa ttcgcaaatc cggtaggtga acccgcggtt gacttttaga tttttttat     720
tatcaacaac aacgtccgcc cggccgcta gttatgtatg tatttgtaaa tgtaatctca     780
aaccgttcct gttggatcga catttaatat gtttaagtga attaattaac gtataacagt     840
cataagaaaa tattgcaata aaatcccatc atttattctt tagagacaat ataaccaaac     900
aacaataaga atcagaatgt aattactcta cattgttcat gataggggtt taactatgat     960
attgttttaa ttctatagga ttcattactt tatcattttg tcaatattta aaattgttta    1020
tttgaaatag ttaacgacat tacaaagttt tcgtataaaa gggcgccaaa gtctggtctc    1080
```

```
attatcagtt cggttccagc tctcataacc                                      1110
```

<210> SEQ ID NO 19
<211> LENGTH: 634
<212> TYPE: DNA
<213> ORGANISM: Bombyx mori
<220> FEATURE:
<223> OTHER INFORMATION: fibroin L chain promoter

<400> SEQUENCE: 19

```
ggtacggttc gtaaagttca cctgcggcta tattcagact cgccaagtta cgtcagtcgt     60
attgtaatga gcgatttagt gggcaacttc attctgttaa ttttgtgtca cggtgcgcgc    120
gcatcgtaaa atttcactct catagatttt tcataacgtg cctaaagaag tataacttca    180
ataatttaaa ttaaaaaaaa acatgcatag aataattata tgaattattt aaaatgtcat    240
ttaccgacat tgacataaca gacgacgtta acactacaaa acatttttaat tccacattgc   300
tacatattca acagttaaat ttgcgttaat tctcgatgcg aacaaatata agaacaatcg    360
gatcaattag atcgctttgt ttcgagcaac acttagttta actagaggcg tacacctcaa    420
gaaatcatct tcattagaaa ctaaaccttta aaatcgcatt aataaagcat agtcaatttt   480
aactgaaatg caaaatcttt tgaacgttag atgctgtcag cgttcgttgg tacagttgtt    540
tgatatttat tttaattgtc tttttatata taaatagtgg aacattaatc acggaatcct    600
gtatagtata taccgattgg tcacataaca gacc                                634
```

<210> SEQ ID NO 20
<211> LENGTH: 1110
<212> TYPE: DNA
<213> ORGANISM: Antheraea pernyi
<220> FEATURE:
<223> OTHER INFORMATION: fibroin L chain promoter

<400> SEQUENCE: 20

```
tccagcgtta ccaatgagag cgcttcaaaa ttctttacaa cttcattaga atacgtcgat     60
ttttctctac ttcatataaa tattctatag atgtgtttgc tataacataa atacttttaa    120
aaaaatgtct caacggttgt gaaaactgtc aaaatctgtt gcgtagttca gaaaaactaa    180
ggaaacatac agaaaattta ttttacaaaa gtacggagat atataaaaat atttcgatta    240
ctttagaatt acaataaaac tatttgacaa tttgattgca aatatagacc atgacaacac    300
cacatctttg ttatctaaaa cacgtagcga caacactcct tgaacgttgt tcgaggatta    360
ctacgataat tggcggtttt ttttccgcac cgcaagaaaa gagtagaaat gtaccgtatt    420
taaatccagt gcggaaattt tcacgcagaa tgcgtttcca tacaattcta taggttacat    480
atcttgcgga aataaattcg tgccaaaaag ccgaagtgcg gggactaata aagatttat    540
ttggcattcc ttctaaccttt tagatataaa tttctgtacg cgcgtatgtc actgaactcc   600
ccctaaacgg ctggactaat tttgatgaaa tattgtttgt gtgttctagt ggatccgaga    660
attgtttaaa ttcgcaaatc cggtaggtga acccgcggtt gacttttaga ttttttttat    720
tatcaacaac aacgtccgcc cggcccgcta gttatgtatg tatttgtaaa tgtaatctca    780
aaccgttcct gttggatcga catttaatat gtttaagtga attaattaac gtataacagt    840
cataagaaaa tattgcaata aaatcccatc atttattctt tagagacaat ataaccaaac    900
aacaataaga atcagaatgt aattactcta cattgttcat gataggggtt taactatgat    960
attgttttaa ttctatagga ttcattactt tatcattttg tcaatattta aaattgttta    1020
```

```
tttgaaatag ttaacgacat tacaaagttt tcgtataaaa gggcgccaaa gtctggtctc   1080
attatcagtt cggttccagc tctcataacc                                    1110
```

<210> SEQ ID NO 21
<211> LENGTH: 1344
<212> TYPE: DNA
<213> ORGANISM: Bombyx mori
<220> FEATURE:
<223> OTHER INFORMATION: p25 promoter

<400> SEQUENCE: 21

```
aagcttagat aattcggcat tgtgcgccac tgagtcgcat tatgctctgt aattggaaac     60
taccaaacat tgtgtaccct ttaatgatat tctaatctat atatataaaa atgaattgct    120
gttcgttagt ctcgctaaaa ctcgagaacg gccggaccga tttggctaat tttggtcttg    180
aattatttgt ggaagtccag agaagattta gaaggtttaa ataaatatga aaatgctcgg    240
aattaaataa aaataacaat tttgtttttt ctttgatgtg ttcccgtcgg acggattcct    300
ttagtctttt atttatcgac tagcgacccg ccgcttcgct tcggaaacat taaaatacac    360
atgataccaa aaaattaaa taattttttt ttaaaaaaag tagcctatgt tcatcaggta    420
caatgtcggc ttcaatgga aaagaattt ttcaaatcgg tccagtagtt tcggagccta     480
ttcgaaacaa acaaacaaac aaatcttttcc tctttataat attagtatag atagtataga    540
ttgaggcact acgaagtctg ccgggtcagc tagtatactc ataaataagg tcgacatctg    600
ttgatgatgg tgatatcttc aaaattacct tagcgcaatg tagacttata cagtatttct    660
gttttcctaa gttaattacc gctgtagcca ataccgtctt taccataagc gcacacgggg    720
cccggtccag ggccgagtgt cgtcgagggg gcccgaaaga ccggcaagtt ctctcacacg    780
tttattccca aaacattttt gtcgggcaca ttacactttt tccacaaatc cgtaatcaga    840
aggtatttag caaggcatat actatgccta taatagaaga ttttgctcaa cagaaatccc    900
gagagaaacc gttatcgaaa tcgtaaccaa aaaaccagca gcattctaat atcattaatg    960
acatattata tcatactgta tttgattacc tataataaag ggtcatactc agtaaaaaaa   1020
tgttaatata attcgctttt tttactttcc aaaagggcct caaattcttg tgtgtccaag   1080
ggccccatct tagtttaaga cgtccctggc tgtagcccag ttactgccac acaaacatgc   1140
ttaactcgcg ccgcctacgt cgaggagaac attttgcgcc ttagaaaata aaatggcgtc   1200
gccgcggcgc aacaataaga acttaattcg tgcaattgtt tccacgacgc tatttattta   1260
acgttattcg ttgtgaggaa caatactttg tataattaat gttgatcagt gcctaacgac   1320
gcagttgttt attattcgcg caac                                         1344
```

<210> SEQ ID NO 22
<211> LENGTH: 244
<212> TYPE: DNA
<213> ORGANISM: Bombyx mori
<220> FEATURE:
<223> OTHER INFORMATION: hsp70 terminator

<400> SEQUENCE: 22

```
aatgaatcgt agatactgaa aaccccgca agttcacttc aactgtgcat cgtgcaccat      60
ctcaatttct ttcatttata catcgttttg ccttctttta tgtaactata ctcctctaag    120
tttcaatctt ggccatgtaa cctctgatct atagaatttt ttaaatgact agaattaatg    180
cccatctttt ttttgaccct aaattcttca tgaaaatata ttacgagggc ttattcagaa    240
gctt                                                                244
```

<210> SEQ ID NO 23
<211> LENGTH: 207
<212> TYPE: DNA
<213> ORGANISM: SV40 virus
<220> FEATURE:
<223> OTHER INFORMATION: SV40 terminator

<400> SEQUENCE: 23

```
tcagccatac cacatttgta gaggttttac ttgctttaaa aaacctccca cacctccccc    60
tgaacctgaa acataaaatg aatgcaattg ttgttgttaa cttgtttatt gcagcttata   120
atggttacaa ataaagcaat agcatcacaa atttcacaaa taaagcattt ttttcactgc   180
attctagttg tggtttgtcc aaactca                                       207
```

<210> SEQ ID NO 24
<211> LENGTH: 765
<212> TYPE: DNA
<213> ORGANISM: Eumeta japonica

<400> SEQUENCE: 24

```
atgagagctc tgaccttcgt gatcctgtgc tgcgctttgc agcaatatgc atcagcaaag    60
gcggattggt atgaagattg gaaaaaaaac caaggttcat ttagagaaac agacttagca   120
gacactgacg aatatcaaac agatagtaat ggtacaatgt ttgaaaaaaa acaacaaga   180
aaaagttcg aaaaagatgg aagtactatg gtaaacagtg attccggaga agataaaatt   240
gtacgaactt tcgtcgtgga aactgacgca tcaggacatg aagttattta tgaagaagat   300
gtagtcatta aaaaagttcc aggtaaacgg aagaaagttt cacaggcaaa tgctaaagct   360
agtgctatag cagccagtgt aggtgcgggc gttggagcag cttccgttgc tggtgcagga   420
acaggagctg gctcaggtgc agctggtgga gcaggagcag gtgctgacgc tggcgctgca   480
gccgccgctg cggcagcagc acaagcagca gccgcagctg ctgccgccgc aggtagtggc   540
gctggtgctg gacgagtcgg agcttacgga ccctacggag gtttagcaag cgctggtgct   600
ggtggtgctg gcggagccgg tggtgcaggt ggatacggtg gtgcaagtgt cgtctacgta   660
ggtggcggag gagccggagc aggtgccggt tcaggcgccg gtgctggatc gggtgccgga   720
gcaggagctg gatcaggtgc aggagcaggt ggagcaggag ccgca                   765
```

<210> SEQ ID NO 25
<211> LENGTH: 1023
<212> TYPE: DNA
<213> ORGANISM: Eumeta japonica

<400> SEQUENCE: 25

```
gcaggtgctg gcggcgctgc tggtgctggt ggtgctggcg agccggtgg tgcaggtgga     60
tacggtggtg caggtgtcgt ctacgtaagt gctggaggag ccggagcagg tgccggttca   120
ggcgccggtg ctggatcggg tgccggagca ggagctggat caggtgcagg agcaggtgga   180
gcaggagccg cagccggagc tggtgctggt gctggttcag gtgcaggatc cggttcaggt   240
gcgggcgctg gagcaggttc cggagcagga gcaggttccg gtgctggtgc aggagcagga   300
gctggttcag gtgcagcagg tggagcagga gctggcgctg gcgctggcgc tgcagccgca   360
gccgcagcag cagcagaagc ggcagccgca gctgccgccg ccgctgccgc cgcaggtagt   420
ggagcaggcg ctgaggagc cggaggctac ggagcgggag ctggagcagg tgccggtgca   480
ggtgctggcg gcgcatctgg aggctacggt tcttacggat cgggagttgc agcaggtgcc   540
```

```
ggtgcaggag ctggtgttgg tggtagcagg ggagcaggtg ttggcgctgg tgttggtgct      600
ggttatggct ccgcattgaa ttcaggagcc ggtgccggag caggtgctgg tgctggagct      660
ggtggtgctg caggagctgg tgctggtgca ggagcaggag ctggttcagg tgcagcaggt      720
ggagcaggag ctggcgctgg cgctggcgct gcagccgcag ccgcagcagc agcagaagcg      780
gcagccgcag ctgccgccgc cgctgccgcc gctggaggag ccggaggcta cggagcggga      840
gctggagcag gtgccggtgc aggtgctggc ggcgctggtg gtgctggtgg tgctggcgga      900
gccggtggtg caggtggata cggtggtgca ggtgtcgtct acgtaagtgc tggaggagcc      960
ggagcaggtg ccggttcagg cgccggtgct ggatcgggtg ccggagcagg agctggatca     1020
ggt                                                                  1023

<210> SEQ ID NO 26
<211> LENGTH: 333
<212> TYPE: DNA
<213> ORGANISM: Eumeta japonica

<400> SEQUENCE: 26
ggtgctggcg gcgcatctgg aggctacggt tcttacggat cgggagttgc agcaggtgcc       60
ggtgcaggag ctggtgttgg tggtagcagg ggagcaggtg ttggcgctgg tgttggtgct      120
ggttatggct ccgcattgaa ttcaggagcc ggtgccggag caggtgctgg tgctggagct      180
ggtggtgctg caggagctgg tgctggtgca ggagcaggag ctggcgctgg agctggattc      240
gcttcttatg aagaccagg tgttcgtgga tgtcaactgt ctcgtaaata cctttttggtt      300 aaagttggtt taagatccac atgctcagat tgt                                  333

<210> SEQ ID NO 27
<211> LENGTH: 29
<212> TYPE: DNA
<213> ORGANISM: Artificial
<220> FEATURE:
<223> OTHER INFORMATION: EvHFB-F21 primer

<400> SEQUENCE: 27
catcagcaaa ggcggattgg tatgaagat                                        29

<210> SEQ ID NO 28
<211> LENGTH: 29
<212> TYPE: DNA
<213> ORGANISM: Artificial
<220> FEATURE:
<223> OTHER INFORMATION: EvHFB-R26 primer

<400> SEQUENCE: 28
ggctcctcca gcacttacgt agacgacac                                        29

<210> SEQ ID NO 29
<211> LENGTH: 26
<212> TYPE: DNA
<213> ORGANISM: Artificial
<220> FEATURE:
<223> OTHER INFORMATION: EvHFB-F26 primer

<400> SEQUENCE: 29
tgtcgtctac gtaggtggcg gaggag                                           26

<210> SEQ ID NO 30
<211> LENGTH: 30
<212> TYPE: DNA
<213> ORGANISM: Artificial
```

```
<220> FEATURE:
<223> OTHER INFORMATION: EvHFB-R12 primer

<400> SEQUENCE: 30
atttacgaga cagttgacat ccacgaacac                                          30

<210> SEQ ID NO 31
<211> LENGTH: 25
<212> TYPE: DNA
<213> ORGANISM: Artificial
<220> FEATURE:
<223> OTHER INFORMATION: EvHFB-F12 primer

<400> SEQUENCE: 31
cagcaaaggc ggattggtat gaaga                                               25

<210> SEQ ID NO 32
<211> LENGTH: 32
<212> TYPE: DNA
<213> ORGANISM: Artificial
<220> FEATURE:
<223> OTHER INFORMATION: EvHFB-F31 primer

<400> SEQUENCE: 32
gctagatcta tagcagccag tgtaggtgcg gg                                       32

<210> SEQ ID NO 33
<211> LENGTH: 33
<212> TYPE: DNA
<213> ORGANISM: Artificial
<220> FEATURE:
<223> OTHER INFORMATION: EvHFB-R31 primer

<400> SEQUENCE: 33
cctggtcttc cataagagtc gactccagct cca                                      33
```

RECOMBINANT BAGWORM SILK

CROSS-REFERENCE TO RELATED APPLICATIONS

This application is a 371 of PCT/JP2017/037327, filed Oct. 16, 2017, which claims benefit of Japanese Patent Application No. 2016-204592 filed on Oct. 18, 2016.

TECHNICAL FIELD

The present invention relates to a modified bagworm silk and a transgenic silkworm that spins the silk, both of which are produced using transgenic technology.

BACKGROUND ART

Threads consitituting insect cocoons and hairs of mammals have been used as animal fibers for clothes and the like since ancient times. Especially silks from silk moth (*Bombyx mori*) larvae, namely a silkworm, (herein often referred to as "silkworm silks") has excellent properties for absorption and desorption of moisture, moisture retention, and heat retention, and also has a unique gloss and smooth texture, and these features make silk a valuable and expensive natural material even today.

However, there exist animal fibers in nature having properties comparable or superior to those of silkworm silks. For example, one of such fibers is the thread spun by a basket worm (alias "bag worm"; the thread is herein often referred to as "bagworm silk"). The bagworm is a general term referring to larvae of moths belonging to the family Psychidae in the order Lepidoptera and are known to spend the entire larval stage living with spindle-shaped or cylinder-shaped nests (bag nests) made of pieces of leaves and twigs and assembled with threads (FIG. 1). For example, the larvae usually hide themselves inside the nests and move with the nests even during feeding.

The silk of bagworm has mechanical properties superior to those of silkworm silk. For example, bagworm silks from *Eumeta minuscula* have an elastic modulus up to 3.5 times of that of silkworm silks, and have a very high strength (Non-Patent Literatures 1 and 2). Additionally, a single fiber of bagworm silk has a cross-sectional area only about one-seventh of that of a single fiber of silkworm silk, which allows production of fine, thin and light fabrics with a smooth texture. Moreover, the bagworm silk has a gloss and a shiny appearance comparable or superior to those of silkworm silk. Thus, the bagworm silk can be an animal fiber which is highly promising as a novel natural material.

However, there are several problems in practical use of the bagworm silk. One of the problems is a problem with mass production. Products using bagworm silk have been just, as it were, handmade a la carte products, such as purses or sandals, which are manufactured by joining together bagworm nests collected from the natural environment. For practical use of the bagworm silk, it is indispensable to obtain a large number of bagworm nests as a material. However, the number of bagworm nests that can be collected in the field is not sufficient for mass production. Thus, it is essential to establish methods for rearing bagworms on a large scale and for efficiently collecting bagworm silks. However, the industry of bagworm silk has just started, and facilities and systems for mass production of the bagworm silk such as rearing facilities, trees for feeding bagworms, and reeling factories, have not yet been sufficiently established. In view of the current situation, it will take a long time to achieve mass production of the bagworm silk.

For practical use of the bagworm silk, another important problem is that pieces of, for example, leaves and twigs are attached on the surface of bagworm nests. These contaminants have to be completely removed for commercialization of bagworm silk. However, the removing work requires enormous labor and cost, thus resulting in a new problem involving increased production cost. Additionally, complete removal of the contaminants is difficult with existing techniques, which leads to decreasing the quality of final products due to, for example, contamination of final products with a small amount of small pieces of leaves as well as light-brown staining of silks with pigments from the contaminants.

However, all of the above problems can be resolved using transgenic silkworm technology. Transgenic technology can be used to produce a useful protein in a host cell by introducing a cloned foreign gene into the host. Conventionally, hosts such as *Escherichia coli* and *Saccharomyces cerevisiae* have been mainly used as hosts of protein production system, but these hosts have a problem that a protein of interest cannot be produced on a large scale in these hosts. Thus, a large-scale protein production system using silkworm as a host has recently been drawing attention. Silkworms (*Bombyx mori*) can synthesize large amounts of protein in the silkgland within a short period of time. Techniques for introducing a foreign gene into host cells to produce transformants are essential in transgenic technology and, in the case of silkworm, a technique of producing recombinant silkworms (transgenic silkworms) has already been established, in which the piggyBac transposon is used to stably maintain foreign genes in the genome (Non-Patent Literature 3).

Morphologically, the silkgland of silkworm consists of a bilateral pair of organs as shown in FIG. 2, each of which is composed of three regions: the anterior silkgland, the middle silkgland, and the posterior silkgland. In the posterior silkgland cells, three major proteins constituting fibroin, a fibrous component of silk, are synthesized, namely fibroin H chain (herein often referred to shortly as "Fib H"), fibroin L chain (herein often referred to shortly as "Fib L"), and p25/FHX (hereinafter referred to as "p25"). These three proteins form a complex (silk fibroin elementary unit; hereinafter referred to as "SFEU complex") and the resulting complex is secreted into the posterior silkgland lumen. In addition, in the middle silkgland cells, a water-soluble gelatin-like protein, sericin, is synthesized, which is a covering component of silk. After the synthesis, sericin is secreted into the middle silkgland lumen. The SFEU complex secreted into the posterior silkgland lumen transitions to the middle silkgland lumen, where the SFEU complex is coated with sericin, and the coated complex is spun as silk from the anterior silkgland (Non-Patent Literature 4).

Similarly to silkworm silk, the bagworm silk is considered to have a basic structure composed of fibroin, which is a fibrous component, and sericin, which is coated over fibroin. Thus, if the silkgland of silkworm can be used as an expression system for the bagworm silks and silkworms can spin the bagworm silks, a large quantity of bagworm silks can be readily obtained. Additionally, if bagworm silks can be collected as silkworm cocoons, contaminants such as those in bagworm nests will not be contained. Furthermore, if the cultured subject is a transgenic silkworm, an existing rearing facility, reeling factory, and rearing technique for silkworms can be directly used, which will enable the practical use soon.

However, the method of producing bagworm silks using the transgenic silkworm described above also has a problem that inhibits its realization. For using transgenic silkworm technology, cloning of the individual genes encoding the component proteins of the bagworm silks, at least cloning of a gene encoding Fib H, which is a major component of fibroin in the bagworm silk, namely a Fib H gene, is essential. However, since Fib H generally has an amino acid sequence in which clusters of glycine and alanine residues are repeated, it is difficult to isolate and identify a gene encoding a full-length bagworm Fib H (hereinafter often referred to as "a bagworm Fib H gene") by conventional cloning techniques. Indeed, the fibroin H chain gene of the bagworm has not been identified so far.

CITATION LIST

Non-Patent Literature

Non-Patent Literature 1: Shigeyosi Ohsaki, 2002, Sen'i Gakkaishi (Sen'i To Kogyo), 58: 74-78.
Non-Patent Literature 2: Gosline J. M. et al., 1999, 202, 3295-3303.
Non-Patent Literature 3: Tamura T. et al., 2000, Nat Biotechnol, 18: 81-84.
Non-Patent Literature 4: Inoue S. et al., 2000, The Journal of Biological Chemistry, 275 (51): 40517-40528.

SUMMARY OF INVENTION

Technical Problem

An object of the present invention is to produce a transgenic silkworm that spins bagworm silks by using transgenic technology, and to provide a method of producing a large quantity of bagworm silks.

Solution to Problem

Identification and cloning of genes encoding the individual components of the bagworm silk are required to produce a transgenic silkworm that spins bagworm silks, but any of the genes encoding these components has not been identified. In addition, cloning the full-length of a gene encoding a bagworm Fib H, which is a major component of the bagworm silk, using conventional techniques, is difficult as described above.

Thus, the present inventors performed transcriptome analysis on *Eumeta japonica* using a next-generation DNA sequencer and successfully cloned a gene fragment encoding a bagworm Fib H-like polypeptide comprising a partial amino acid sequence of bagworm Fib H. Then, the gene fragment was fused with a gene fragment encoding Fib H derived from silkworm to produce a gene encoding a full-length form of modified bagworm Fib H (hereinafter often referred to as "modified bagworm Fib H gene"). In addition, the gene was introduced into silkworm to produce a transgenic silkworm. The transgenic silkworm spins a modified bagworm silk comprising Fib H and silkworm-drived Fib L, p25 and sericin, wherein the Fib H comprises the modified bagworm Fib H in a portion of silkworm Fib H. The modified bagworm silk is a hybrid silk in which the physical properties of bagworm silk have been imparted to silkworm silk. The present invention is based on the above-described research results and provides the following.

(1) A gene encoding a modified bagworm fibroin H chain comprising a plurality of the amino acid sequence shown in SEQ ID NO: 1.
(2) The gene according to (1), wherein the modified bagworm fibroin H chain comprises any of: the amino acid sequence shown in SEQ ID NO: 5; an amino acid sequence derived from the amino acid sequence shown in SEQ ID NO: 5 having an addition, a deletion, or a substitution of one or a plurality of amino acid(s); or an amino acid sequence having an amino acid identity of 90% or more to the amino acid sequence shown in SEQ ID NO: 5.
(3) The gene according to (2), wherein the modified bagworm fibroin H chain comprises any of: the amino acid sequence shown in SEQ ID NO: 7; an amino acid sequence derived from the amino acid sequence shown in SEQ ID NO: 7 having an addition, a deletion, or a substitution of one or a plurality of amino acid(s); or an amino acid sequence having an amino acid identity of 90% or more to the amino acid sequence shown in SEQ ID NO: 7.
(4) The gene according to any one of (1) to (3), comprising a portion of the gene encoding a silkworm fibroin H chain.
(5) The gene according to (4), wherein the modified bagworm fibroin H chain encodes any of: the amino acid sequence shown in SEQ ID NO: 9; an amino acid sequence derived from the amino acid sequence shown in SEQ ID NO: 9 having an addition, a deletion, or a substitution of one or a plurality of amino acid(s); or an amino acid sequence having an amino acid identity of 90% or more to the amino acid sequence shown in SEQ ID NO: 9.
(6) An expression vector of a modified bagworm fibroin H chain gene, the vector comprising a promoter for expression in the posterior silkgland derived from a silk spinning insect and the modified bagworm fibroin H chain gene according to any one of (1) to (5) in a state that allows for the expression in a silkworm cell, wherein said modified bagworm fibroin H chain gene is placed such that the expression thereof is directly or indirectly controlled by said promoter for expression in the posterior silkgland.
(7) The expression vector of a modified bagworm fibroin H chain gene according to (6), comprising the promoter for expression in the posterior silkgland derived from a silk spinning insect and the modified bagworm fibroin H chain gene according to any one of (1) to (5), wherein the gene is placed under the downstream control of the promoter.
(8) The expression vector of a modified bagworm fibroin H chain gene according to (6), wherein the expression vector is composed of: a first expression unit comprising a promoter for expression in the posterior silkgland derived from a silk spinning insect and a gene encoding a transcriptional regulator placed under the downstream control of the promoter; and a second expression unit comprising a promoter targeted by the transcriptional regulator and the modified bagworm fibroin H chain gene placed under the downstream control of the targeted promoter.
(9) The expression vector of a modified bagworm fibroin H chain gene according to (8), wherein the gene encoding the transcriptional regulator is a GAL4 gene and the promoter targeted by the transcriptional regulator is a UAS promoter.
(10) The expression vector of a modified bagworm fibroin H chain gene according to any one of (6) to (9), wherein the promoter for expression in the posterior silkgland is a posterior silkgland-specific promoter.

(11) The expression vector of a modified bagworm fibroin H chain gene according to (10), wherein the posterior silkgland-specific promoter is a promoter of any of fibroin H chain, fibroin L chain, or p25.

(12) The expression vector of a modified bagworm fibroin H chain gene according to any one of (6) to (11), wherein the silk spinning insect is a silkworm.

(13) A transgenic silkworm comprising the expression vector a modified bagworm fibroin H chain gene according to any one of (6) to (12).

(14) A method of producing a transgenic silkworm that spins a modified bagworm silk, the method comprising the steps of: introducing the expression vector of a modified bagworm fibroin H chain gene according to any one of (6) or (7) or (10) to (12) depending therefrom into a host silkworm; and selecting a transgenic silkworm comprising the expression vector.

(15) A method of producing a transgenic silkworm that spins a modified bagworm silk, the method comprising the steps of: crossing a transgenic silkworm having the first expression unit according to any one of (8) or (9) or (10) to (12) depending therefrom and a transgenic silkworm having the second expression unit according to any one of (8) or (9) or (10) to (12) depending therefrom; and selecting a transgenic silkworm having the first and second expression units from progenies after the cross.

(16) A method of producing a modified bagworm silk, the method comprising the steps of: allowing the transgenic silkworm according to (13) to cocoon; collecting the cocoon; and reeling the modified bagworm silk from the collected cocoon.

(17) A modified bagworm silk spun by the transgenic silkworm according to (13).

The present description incorporates the disclosure of Japanese Patent Application No. 2016-204592 to which the present application claims priority.

Advantageous Effects of Invention

According to the expression vector of the present invention, a transgenic silkworm that spins a modified bagworm silk can be produced by introducing the expression vector into a silkworm.

Also, the transgenic silkworm of the present invention can be used to produce a modified bagworm silk in which the physical properties of bagworm silk are artificially imparted to silkworm silk.

DESCRIPTION OF EMBODIMENTS

1. A Modified Bagworm Fibroin H Chain Gene
1-1. Summary

The first aspect of the present invention is a gene encoding a modified bagworm Fib H having a portion of the amino acids of the fibroin H chain (Fib H) in the bagworm silk derived from *Eumeta japonica* (a modified bagworm Fib H gene). By introducing the gene of the present invention to a silkworm and allowing the gene to be expressed in the posterior silkgland, it is possible to allow the transgenic silkworm to spin a hybrid silk having the physical properties of bagworm silk derived from *Eumeta japonica*, namely a modified bagworm silk.

1-2. Definition

The following terms frequently used herein are defined as follows.

The term "bagworm" collectively refers to a moth larva belonging to the family Psychidae in the order Lepidoptera, as described above. The bagworm described herein is not limited to a particular type as long as bagworm silks spun by the bagworm comprise the below-described amino acid sequence shown in SEQ ID NO: 1. Since Fib H subjected to the gene cloning herein is a Fib H from *Eumeta japonica*, the bagworm is preferably a larva of the genus *Eumeta*, such as *Eumeta japonica* and *Eumeta minuscula*, more preferably a larva of *Eumeta japonica*.

The term "silk" as used herein refers to a thread derived from an insect, which is a proteinous thread spun by a larva or an adult of the insect for the purpose of nest building, migration, anchoring, cocooning, prey capture, and the like. Reference to the term "silk" with no modifier herein in principle means a quite ordinary silk wherein the origin of the silk is not specified with an insect name. In case of indicating a silk from a particular insect, the name of the organism is placed before the term "silk," as seen in silkworm silk or bagworm silk.

Figure 1:
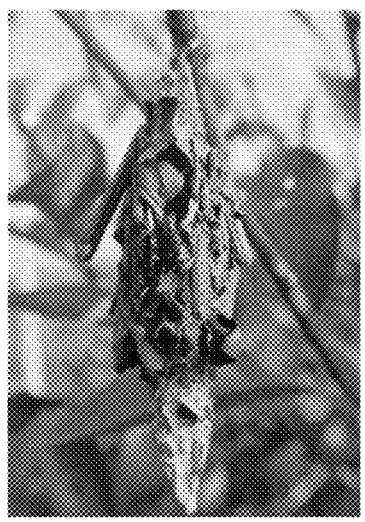
FIG. 1A shows the appearance of a nest of a bagworm of *Eumeta japonica* (a *Eumeta japonica* bagworm).
FIG. 1B shows the inside of the nest of a *Eumeta japonica* bagworm, which has been cut and opened along the longitudinal axis.
Figure 1:
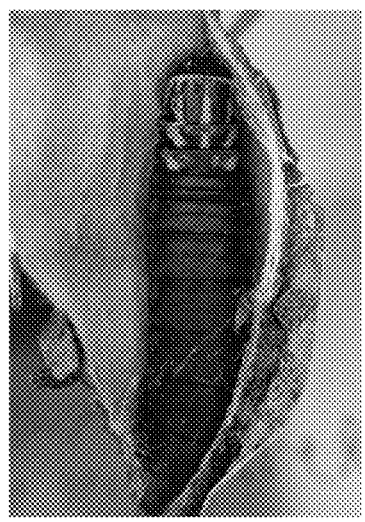
Figure 2:
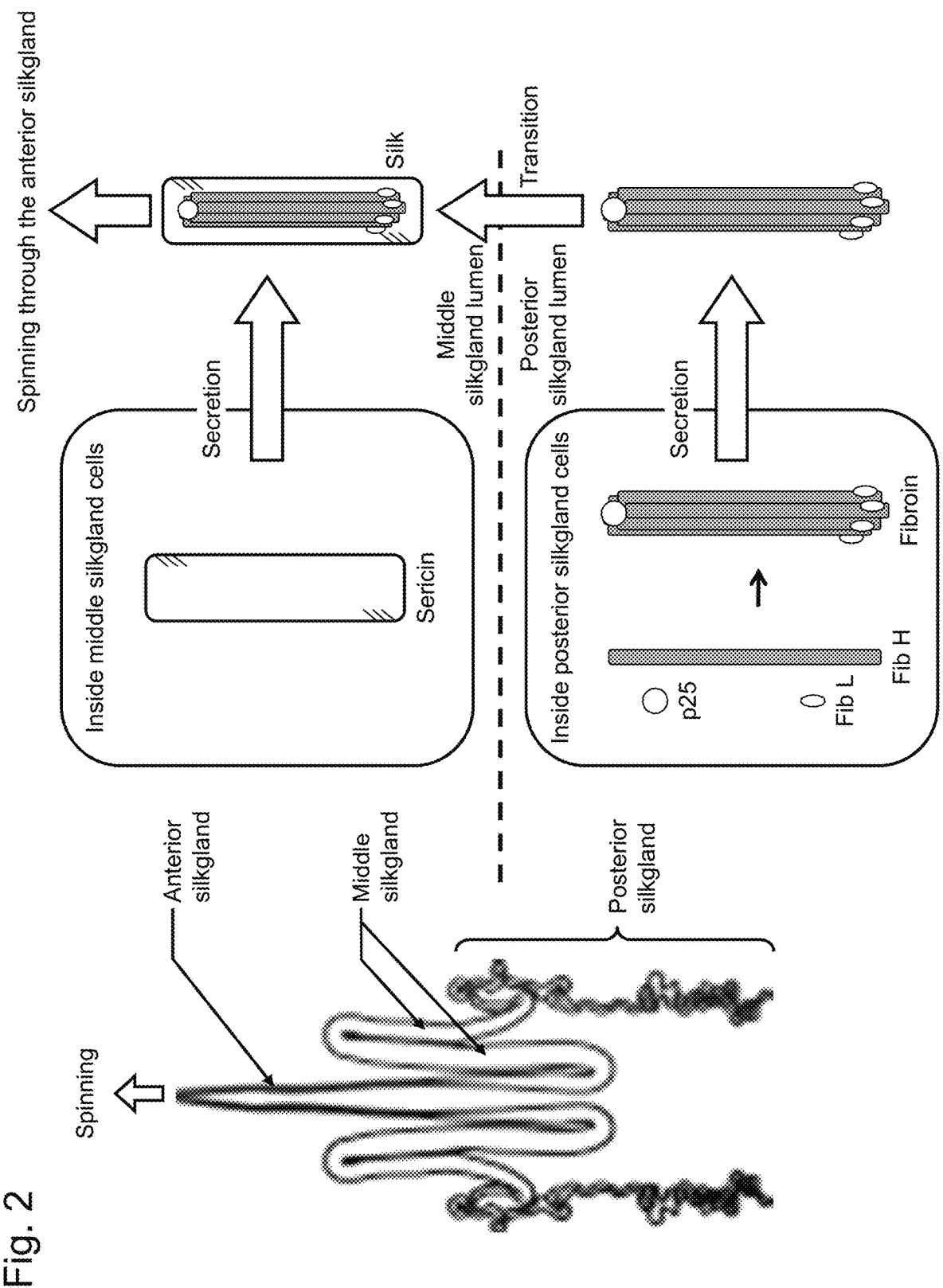
FIG. 2 is a schematic diagram showing the silkgland of silkworm, the constituent proteins of fibroin expressed in each region of the silkgland, and processes until spinning silk.

The term "silkgland" refers to a tubular organ which is derived from the salivary gland and has functions of producing, storing, and also secreting liquid silk. Silkglands are normally present as a bilateral pair along the digestive tract of an insect, mainly a larva of an insect, capable of spinning silks, and each silkgland is composed of three regions: anterior, middle, and posterior silkglands. FIG. 2 depicts the silkgland of silkworm, and the silkgland of bagworm has a nearly identical morphology to that of silkworm. As described above, the posterior silkgland produces and secretes fibroin, a fibrous component of silk. Additionally, the middle silkgland produces and secretes sericin, a covering component, and its lumen stores sericin together with fibroin which has been transitioned from the posterior silkgland.

The term "fibroin H chain (Fib H)" refers to one of the proteins constituting fibroin, a fibrous protein component of silk. As shown in FIG. 2, fibroin of silkworm, for example, is mainly composed of three proteins: Fib H, Fib L, and p25. Among these proteins, Fib H is a major constituent protein of fibroin and the properties of silk are mainly attributed to Fib H. Herein, the origin of Fib H is in principle not limited to a particular insect by reference to the term "Fib H" with no modifier. On the other hand, in case of indicating Fib H from a particular insect, the name of the organism is placed before the term "Fib H," as seen in silkworm Fib H or bagworm Fib H.

The term "modified Fib H" as used herein refers to an artificially modified Fib H, which is composed of an amino acid sequence different from that of the wild-type Fib H. Examples of the modified Fib H include a mutant Fib H derived from the amino acid sequence of Fib H having an addition, a deletion and/or a substitution of one or a plurality of amino acids, and a chimeric Fib H obtained by a fusion of amino acid sequences of Fib H drived from insects of two or more different species.

The term "modified bagworm Fib H" as used herein refers to a modified Fib H in bagworm-derived Fib H, and comprises a mutant Fib H derived from the amino acid sequence of wild-type bagworm Fib H having an addition, a deletion and/or a substitution of one or a plurality of amino acids, and a chimeric Fib H obtained by a fusion of amino acid sequences of Fib H drived from insects of two or more different species.

The term "fibroin H chain (Fib H) gene" as used herein refers to a gene encoding the above-described Fib H. Similarly to Fib H, the origin of Fib H gene is herein in principle not limited to a particular insect by reference to the term "Fib H gene" with no modifier. On the other hand, in case of indicating a Fib H gene from a particular insect, the name of the organism is placed before the term "Fib H," as seen in silkworm Fib H gene or bagworm Fib H gene.

In addition, the term "modified Fib H gene" as used herein refers to a gene encoding the above-described modified Fib H. Thus, the term "modified bagworm Fib H gene" refers to a gene encoding a modified Fib H in a bagworm-derived Fib H. The present aspect is directed to the modified bagworm Fib H gene.

The term "modified bagworm silk" as used herein refers to a silk spun by a transgenic silkworm obtained by introduction of the above-described modified Fib H gene in a state that allows for expression in the posterior silkgland of silkworm. All of the modified bagworm silk except for Fib H are composed of silkworm-derived silk components. In other words, Fib H in the modified bagworm silk is a hybrid Fib H wherein endogenous silkworm Fib H and modified bagworm Fib H are mixed. Thus, the modified bagworm silk is, as it were, a hybrid silk of silkworm silk and the modified bagworm silk. The hybrid silk has the physical properties of bagworm silk since the silkworm Fib H and the modified bagworm Fib H are mixed therein.

1-3. Configuration

In general, Fib H comprises one or a plurality of a repeat unit in the amino acid sequence. Herein, the "repeat unit" refers to an amino acid sequence comprising a number of glycine (G) and alanine (A) residues and appearing once or multiple times in the amino acid sequence of Fib H. The modified bagworm Fib H encoded by the modified bagworm Fib H gene of the present invention also comprises one or a plurarity of the repeat unit in the amino acid sequence.

The modified bagworm Fib H comprises, as a "repeat unit," the amino acid sequence shown in SEQ ID NO: 5; an amino acid sequence derived from the amino acid sequence shown in SEQ ID NO: 5 having an addition, a deletion, or a substitution of one or a plurality of amino acids; or an amino acid sequence having an amino acid identity of 90% or more, 93% or more, 95% or more, 97% or more, 98% or more, or 99% or more to the amino acid sequence shown in SEQ ID NO: 5. The amino acid sequence shown in SEQ ID NO: 5 is an amino acid sequence comprising a portion of the wild-type bagworm Fib H of *Eumeta japonica*. The term "a plurality of" or "multiple" as used herein refers to 2 to 10, 2 to 8, 2 to 6, 2 to 5, 2 to 4, or 2 to 3. Additionally, the above-described amino acid substitution is preferably a conservative amino acid substitution because a protein carrying a conservative amino acid substitution can have a structure or properties substantially comparable to those of a wild-type protein. Conservative amino acid means the relationship among amino acids classified into the same amino acid group. The following groups are known as the above-described amino acid groups: non-polar amino acid group (glycine, alanine, phenylalanine, valine, leucine, isoleucine, methionine, proline, tryptophan); polar amino acid group (amino acids other than non-polar amino acids); charged amino acid group (acidic amino acids (aspartic acid, glutamic acid) and basic amino acid group (arginine, histidine, lysine)); uncharged amino acid group (amino acids other than charged amino acids); aromatic amino acid group (phenylalanine, tryptophan, tyrosine); branched amino acid group (leucine, isoleucine, valine); aliphatic amino acid group (glycine, alanine, leucine, isoleucine, valine); and the like. Furthermore, the term "amino acid identity" as used herein refers to the ratio (%) of the number of identical amino acids in one polypeptide to the total number of amino acids in the other polypeptide, when the amino acid sequences of the two polypeptides are aligned with introducing gaps, if necessary, into either amino acid sequence such that the the highest degree of match between the two is obtained The % of amino acid identity can be easily determined using a known program such as the homology search program BLAST (Basic local alignment search tool; Altschul, S. F. et al., J. Mol. Biol., 215, 403-410, 1990) search.

Specific examples of the base sequence of a polynucleotide encoding the above-described repeat unit include the base sequence shown in SEQ ID NO: 6, which encodes the amino acid sequence shown in SEQ ID NO: 5.

The modified bagworm Fib H encoded by the modified bagworm Fib H gene of the present invention comprises a plurarity of, for example two or more, preferably three or more core sequences in the above-described repeat unit. The "core sequence" herein refers to a sequence consisting of about a dozen of amino acids, which further repeats multiple times within the repeat unit.

Examples of the "core sequence" in the modified bagworm Fib H include the amino acid sequence composed of 13 amino acids shown in SEQ ID NO: 1 (GAGAGAGSGAGAG). The amino acid sequence is a partial amino acid sequence of the wild-type bagworm Fib H of *Eumeta japonica*. The repeat unit consisting of the amino acid sequence shown in the above-described SEQ ID NO: 5 comprises three core sequences.

Specific examples of the base sequence of a polynucleotide encoding the above-described core sequence include the base sequences shown in SEQ ID NOs: 2, 3, and 4, each of which encode the amino acid sequence shown in SEQ ID NO: 1.

The modified bagworm Fib H encoded by the gene of the present invention can further comprise the amino acid sequence shown in SEQ ID NO: 7; an amino acid sequence derived from the amino acid sequence shown in SEQ ID NO: 7 having an addition, a deletion, or a substitution of one or a plurality of amino acids; or an amino acid sequence having an amino acid identity of 90% or more to the amino acid sequence shown in SEQ ID NO: 7. The amino acid sequence shown in SEQ ID NO: 7 is an amino acid sequence comprising a portion of the wild-type bagworm Fib H of *Eumeta japonica*. One copy of the above-described repeat unit is contained in the amino acid sequence shown in SEQ ID NO: 7, but the number of the repeat unit may be increased to two or more, as necessary. Specific examples of the base sequence encoding the amino acid sequence shown in SEQ ID NO: 7 include the base sequence shown in SEQ ID NO: 8.

The modified bagworm Fib H encoded by the gene of the present invention may be a chimeric Fib H with Fib H of other insects, for example a chimeric Fib H between bagworm Fib H and silkworm Fib H. Specific examples include a chimeric Fib H between bagworm Fib H of *Eumeta japonica*, which consists of the amino acid sequence shown in SEQ ID NO: 9, and silkworm Fib H. In the chimeric Fib H, positions 1 to 153 and 466 to 524 are amino acid sequence derived from silkworm Fib H, and positions 156 to 463 comprise amino acid sequence derived from bagworm Fib H of *Eumeta japonica*. Also, the modified bagworm Fib H may be a Fib H consisting of an amino acid sequence derived from the amino acid sequence shown in SEQ ID NO: 9 having an addition, a deletion, or a substitution of one or a plurality of amino acids; or an amino acid sequence having an amino acid identity of 90% or more to the amino acid sequence shown in SEQ ID NO: 9. Furthermore, one copy of the above-described repeat unit is contained in the amino acid sequence shown in SEQ ID NO: 9, but the number of the repeat unit may be increased to two or more, as necessary. Specific examples of the base sequence encoding the amino acid sequence shown in SEQ ID NO: 9 include the base sequence shown in SEQ ID NO: 10.

The modified bagworm Fib H of the present invention may have an exogenous signal peptide at the N-terminal side, as necessary. The "signal peptide" refers to an extracellular transport signal required in extracellularly secreting a protein biosynthesized with gene expression. After translation, signal peptides are cleaved and removed by signal peptidase before extracellular secretion. Signal peptides comprise positively charged amino acids such as Lys and Arg in the N-terminal side, followed by a sequence of amino acids of high hydrophobicity such as Ala, Leu, Val, Ile, Val, and Phe. Secretory proteins usually have an endogenous signal peptide at the N-terminal side thereof. Thus, in cases where a modified bagworm Fib H has an endogenous signal peptide at the N-terminal side thereof, the exogenous signal peptide is not required in an exogenous gene expression vector of this aspect. For example, in a chimeric Fib H between bagworm Fib H composed of the amino acid sequence shown in SEQ ID NO: 9 and silkworm Fib H, the amino acids of positions 1 to 21 correspond to the endogenous signal peptide derived from silkworm Fib H, and thus does not need an exogenous signal peptide. On the other hand, in cases where a modified bagworm Fib H has no signal peptide, an exogenous signal peptide may be placed at the N-terminal. In addition, the C-terminal side of the signal peptide may have a signal sequence post-insertion sequence that promotes the cleavage of the signal peptide and the secretion, and/or an amino acid sequence containing a recognition site for a signal peptidase that cleaves the signal peptide from the fusion protein. The amino acid sequence of the signal peptide is not particularly limited and may usually be in the range of 3 to 60 amino acids.

Examples of the signal peptide DNA encoding a signal peptide include, but are not limited to, a signal peptide DNA encoding the silkworm sericin-1 signal peptide comprising the amino acid sequence shown in SEQ ID NO: 11 (for example, DNA comprising a base sequence shown in SEQ ID NO: 12), a signal peptide DNA encoding the silkworm sericin-2 signal peptide comprising the amino acid sequence shown in SEQ ID NO: 13 (for example, DNA comprising a base sequence shown in SEQ ID NO: 14), and a signal peptide DNA encoding the silkworm sericin-3 signal peptide comprising the amino acid sequence shown in SEQ ID NO: 15 (for example, DNA comprising a base sequence shown in SEQ ID NO: 16).

2. Expression Vector of a Modified Bagworm Fib H Gene 2-1. Summary

The second aspect of the present invention is an expression vector of a modified bagworm Fib H gene. The expression vector of the present invention comprises the modified bagworm Fib H gene according to the first aspect in a state that allows for the expression in the posterior silkgland of silkworm. The expression vector of the present invention can be introduced into a silkworm to obtain modified bagworm silks from the transgenic silkworm.

2-2. Configuration 2-2-1. Components of the Expression Vector of a Modified Bagworm Fib H Gene The "expression vector" as used herein refers to an expression unit comprising a gene encoding a protein of interest and being capable of regulating the expression of the gene.

The expression vector of a modified bagworm Fib H gene of the present invention is configured such that the modified bagworm Fib H gene can be expressed in the posterior silkgland of a host silkworm.

Various vectors can be used as a parent vector for the expression vector of a modified bagworm Fib H gene. Examples of the parent vector include an expression vector capable of autonomous replication, such as a plasmid or a bacmid; a viral vector; or an expression vector which is capable of homologous or non-homologous recombination into the chromosome, or a portion of the host chromosome in which the expression vector is inserted into the chromosome. In addition, shuttle vectors which are capable of replicating in *Escherichia coli*, *Bacillus subtilis*, or yeasts can also be used.

The expression vector of a modified bagworm Fib H gene comprises a promoter for expression in the posterior silkgland and the modified bagworm Fib H gene as essential components. Additionally, the expression vector of a modified bagworm Fib H gene comprises an optional component such as a marker gene, an inverted terminal repetitive sequence of a transposon, 5'UTR, 3'UTR, a terminator, an enhancer, and an insulator. Further, in cases where the expression vector of a modified bagworm Fib H gene is composed of two gene expression units of the below-described first and second expression units, the expression vector of a modified bagworm Fib H gene comprises a gene of a transcriptional regulator and a promoter targeted by the transcriptional regulator as essential components. The respective components in the expression vector of a modified bagworm Fib H gene of the present invention will be specifically described below.

(1) Promoter for Expression in the Posterior Silkgland

The "promoter for expression in the posterior silkgland" refers to a promoter that can regulate the expression of the downstream gene in the posterior silkgland of silkworm when the expression vector of a modified bagworm Fib H gene of the present invention is introduced in a host silkworm.

The promoter for expression in the posterior silkgland may be a promoter of any gene as long as the promoter of the gene is functional in the posterior silkgland of silkworm. The term "functional" or "operable" means that the promoter can regulate the expression of a downstream gene. Examples of the promoter for expression in the posterior silkgland include a posterior silkgland-specific promoter, a systemic promoter capable of ubiquitous expression, a constitutive-active promoter or a stage-specific promoter, or an inducible promoter. A posterior silkgland-specific promoter is preferred. Among the promoters, a preferred promoter is a promoter of a gene encoding a protein that is specifically expressed in a large amount in the posterior silkgland of a silk spinning insect; particularly preferred is a late final instar stage- and posterior silkgland-specific promoter, which is specifically activated in the posterior silkgland from the late final instar stage to the prepupal stage. For example, the gene promoters for the fibroin constituent proteins Fib H, Fib L, or p25 (herein referred to as "Fib H promoter," "Fib L promoter," or "p25 promoter," respectively) are suitable as a promoter for expression in the posterior silkgland in the expression vector of a modified bagworm Fib H gene of the present invention.

The origin species, namely donor species, of the promoter for expression in the posterior silkgland is not particularly limited as long as the promoter is functional in the cell of the host silkworm. In general, the base sequence of each promoter of Fib H, Fib L or p25 for posterior silkgland-specific expression is evolutionarily conserved very well among silk spinning insects (Sezutsu H., et al., 2009, Journal of Insect Biotechnology and Sericology, 78: 1-10). Therefore, even if the donor of the promoter for expression in the posterior silkgland in the expression vector of a modified bagworm Fib H gene of the present invention is not silkworm, the promoter for expression in the posterior silkgland can be functional in the posterior silkgland of silkworm.

The term "silk spinning insect" as used herein collectively refers to an insect having a silkgland(s) and being capable of spinning silks, and usually an insect species which can spin silks in the larval stage for the purpose of nest building, cocooning, or migration. Specifically, the term refers to species belonging to the orders Lepidoptera, Hymenoptera, Neuroptera, and Trichoptera, preferably species belonging to the order Lepidoptera which can spin a large quantity of silks. The silk spinning insect herein is preferably species belonging to the families Bombycidae, Saturniidae, Brahmaeidae, Eupterotidae, Lasiocampidae, Psychidae, Archtiidae, Noctuidae, and the like. Species belonging to the genera *Bombyx, Sarnia, Antheraea, Saturnia, Attacus*, and *Rhodinia*, specifically *Bombyx mori, Bombyx mandarina, Sarnia cynthia* (including *Sarnia cynthia* ricini, and a hybrid species between *Sarnia cynthia* and *Sarnia cynthia ricini*), *Antheraea yamamai, Antheraea pernyi, Saturnia japonica, Actias gnoma*, and the like are particularly preferred. Thus, the origin species of the promoter for expression in the posterior silkgland in the expression vector of a modified bagworm Fib H gene of the present invention are preferably species belonging to the same order as the host silkworm, namely Lepidoptera; more preferably species belonging to the same family as the host silkworm, namely Bombycidae; still more preferably species belonging to the same genus as the host silkworm, such as *Bombyx mandarina*. The most preferred origin species is the same species as the host silkworm, namely *Bombyx mori*.

As specific examples of the posterior silkgland-specific promoter, the silkworm Fib H promoter comprising the base sequence shown in SEQ ID NO: 17, the *Antheraea pernyi* Fib H promoter comprising the base sequence shown in SEQ ID NO: 18, the silkworm Fib L promoter comprising the base sequence shown in SEQ ID NO: 19, the *Antheraea pernyi* Fib L promoter comprising the base sequence shown in SEQ ID NO: 20, the silkworm p25 promoter comprising the base sequence shown in SEQ ID NO: 21, and the like can be used.

(2) Modified Bagworm Fib H Gene

The modified bagworm Fib H gene is a gene encoding the protein of interest to be expressed, in the expression vector of a modified bagworm Fib H gene in the present invention. Because the details of the gene have been described in the first aspect, a detailed explanation of the gene is omitted here.

In the expression vector of a modified bagworm Fib H gene of the present invention, the modified bagworm Fib H gene is linked to and placed under the direct or indirect control of the promoter for expression in the posterior silkgland described above. The phrase "under the direct control of" as used herein means that the modified bagworm Fib H gene is placed downstream of the promoter for expression in the posterior silkgland and the expression thereof is regulated directly by the promoter for expression in the posterior silkgland. Further, the phrase "under the indirect control of" means that gene expression is regulated by the promoter for expression in the posterior silkgland through other gene expression activities and the like. For example, in cases where the expression vector of a modified bagworm Fib H gene is composed of the two expression units described below, the expression of the modified bagworm Fib H gene is regulated by the promoter for expression in the posterior silkgland through expression of a gene encoding a transcriptional regulator and the activity of a promoter targeted by the transcriptional regulator.

(3) Marker Gene

A "marker gene" is a gene encoding a marker protein, which is also called selection marker. The "marker protein" refers to a polypeptide wherein the presence or absence of expression of the marker gene can be discriminated based on the activity of the polypeptide. A marker gene is used for the purpose of discriminating hosts having the expression vector of a modified bagworm Fib H gene, namely transformants, and/or of monitoring the protein of interest expressed from the expression vector of a modified bagworm Fib H gene. In either case, transformants can be discriminated, or the expression level of the modified bagworm Fib H can be monitored, on the basis of the activity of the marker protein. The phrase "on the basis of the activity" means "on the basis of the result of detection of the activity." The detection of the activity may be direct detection of the activity itself of a marker protein, or indirect detection through detection of a metabolite produced by the activity of the marker protein, such as a pigment. The detection may be any of biological detection (including detections by binding of a peptide or a nucleic acid such as an antibody or an aptamer), chemical detection (including detections based on enzymatic reactions), physical detection (including detections based on behavior analyses), or sensory detection by a detector (including detections by vision, touch sensation, olfaction, audition, or gustation).

The type of the marker protein encoded by the marker gene is not particularly limited as long as the activity of the marker protein can be detected by a technique known in the art. The marker protein is preferably a protein detected with low invasiveness to transformants. Examples thereof include a tag peptide, a fluorescent protein, a chromogenic protein, a luminescent protein, an externally secreted protein, and a protein regulating external morphology. A fluorescent protein, a chromogenic protein, a luminescent protein, and an externally secreted protein are particularly suitable because these proteins can be visually detected under certain conditions without affecting the external morphology of transformants and thus have very low invasiveness to transformants, and allow for easy discrimination and selection of transformants.

The "tag peptide" refers to a short peptide consisting of amino acids ranging from about a dozen to dozens of amino acids which can label a protein, and is used for detection and purification of proteins. Usually, a base sequence encoding a tag peptide is linked to the 5' or 3' terminal side of a gene encoding the protein to be labeled (herein, the modified bagworm Fib H gene), and labelling is performed by expression as a fusion protein with the tag peptide. Any of various tag peptides that have been developed in the art may be used. Specific examples of the tag peptide include FLAG, HA, His, myc, and the like.

The "fluorescent protein" refers to a protein that emits fluorescence at a particular wavelength when irradiated by excitation light at a specific wavelength. The fluorescent protein may be either natural or unnatural. Additionally, the wavelengths of the excitation and emission lights are not limited to particular wavelengths. Specific examples of the fluorescent protein include CFP, RFP, DsRed (including derivatives such as 3xP3-DsRed), YFP, PE, PerCP, APC, GFP (including derivatives such as EGFP and 3xP3-EGFP).

The "chromogenic protein" refers to a protein, usually enzyme, which is involved in pigment biosynthesis. The term "pigment" as used herein refers to a low-molecular-weight compound or peptide that can color transformants. The pigment is not limited to a particular type of pigment. The pigment is preferably a pigment that appears as external color of an individual. Examples of the pigment include melanin-based pigments (including dopamine-melanin), ommochrome pigments, or pteridine pigments.

As used herein, the term "luminescent protein" refers to a substrate protein that is capable of emitting light with no need of excitation light, or an enzyme that catalyzes the light emission of such a substrate protein. Examples of substrate proteins include luciferin or aequorin; and Examples of an enzyme include luciferase.

As used herein, the term "externally secreted protein" refers to a protein that is secreted to the outside of cells or the outside of the body and includes an exocrine enzyme and the like. Examples of the exocrine enzyme include digestive enzymes, as well as enzymes that contribute to degradation or inactivation of agents such as blasticidine and render hosts resistant to the agents.

In the expression vector of a modified bagworm Fib H gene, the marker gene is placed downstream of a promoter in a state that allows for the expression, being linked to or independent of the modified bagworm Fib H gene.

(4) Inverted Terminal Repetitive Sequence of a Transposon

The "inverted terminal repetitive sequence (ITRs) of a transposon" refers to an optional component that can be comprised in the expression vector of a modified bagworm Fib H gene of the present invention when the expression vector is an expression vector capable of homologous recombination with genomic DNA. Two copies of an inverted terminal repetitive sequence are usually used as one set, and piggyBac, mariner, *minos* and the like can be used as a transposon (Shimizu, K. et al., 2000, Insect Mol. Biol., 9, 277-281; Wang W. et al.,2000, Insect Mol Biol 9(2): 145-55).

(5) 5'UTR and 3'UTR

The "5' UTR (5' untranslated region)" and "3' UTR (3' untranslated region)" each refer to a polynucleotide consisting of an untraslated region which does not encode a protein or a fragment thereof, or a functional nucleic acid on its own. The base sequence constituting each UTR is not particularly limited, and is preferably 5' UTR and 3' UTR derived from the Fib H gene. In the expression vector of a modified bagworm Fib H gene, the 5' UTR is placed upstream (on the 5' terminal side) of the start codon of the above-described Fib H gene, while the 3' UTR is placed downstream (on the 3' terminal side) of the stop codon of the Fib H gene. The 3' UTR may comprise a poly(A) signal.

(6) Terminator

The "terminator" refers to a base sequence placed on the 3' side, preferably downstream of the stop codon, of the modified bagworm Fib H gene in the expression vector of a modified bagworm Fib H gene of the present invention, and is composed of a base sequence capable of terminating the transcription of the modified bagworm Fib H gene. Examples of the terminator include the hsp70 terminator consisting of the base sequence shown in SEQ ID NO: 22 and the SV40 terminator consisting of the base sequence shown in SEQ ID NO: 23.

(7) Enhancer

The "enhancer" consists of a base sequence capable of further enhancing the expression of the modified bagworm Fib H gene under the control of a site-specific promoter in the expression vector of a modified bagworm Fib H gene of the present invention.

(8) Insulator

The "insulator" refers to a base sequence wherein the sequence can stably regulate the transcription of a gene placed between the sequences without being influenced by the surrounding chromatin of the chromosome. Examples of the insulator include the chicken cHS4 sequence and the *Drosophila gypsy* sequence.

(9) Gene of a Transcriptional Regulator

The "gene of a transcriptional regulator" is an essential component of the first expression unit described below. The "transcriptional regulator" as used herein refers to a protein factor that can bind to a target promoter as described below and then activates the target promoter. Examples of the transcriptional regulator include the yeast Gal4 protein, a protein for activation of the galactose metabolism; tTA, a tetracycline-controlled transactivator and variants thereof.

(10) Promoter Targeted by a Transcriptional Regulator

The "promoter targeted by a transcriptional regulator" is an essential component of the second expression unit described below and refers to a promoter that can activate expression of a gene under the control of the promoter upon binding of the transcriptional regulator encoded in the first expression unit to the promoter. The above-described transcriptional regulator and the target promoter are mutually related; typically selection of the target promoter necessarily depends on the selection of the transcriptional regulator. For example, in cases where the transcriptional regulator is the Gal4 protein, the UAS (upstream activating sequence) is used.

2-2-2. Unit Organization of the Expression Vector of a Modified Bagworm Fib H Gene The expression vector of a modified bagworm Fib H gene of the present invention may be composed of one expression unit, or may be composed of two expression units. Each case will be described below.

(1) Vector Composed of One Expression Unit

When composed of one expression unit, the expression vector of a modified bagworm Fib H gene comprises all components required to express the modified bagworm Fib H gene in silkworm cells in one vector. Specifically, the vector comprises a promoter for expression in the posterior silkgland and the modified bagworm Fib H gene placed under the control of the promoter, both of which are essential components.

The expression vector of a modified bagworm Fib H gene may comprise two or more copies of the modified bagworm Fib H gene under the control of one promoter.

In cases where the expression vector of a modified bagworm Fib H gene is composed of one gene expression unit, introduction of the expression vector of a modified bagworm Fib H gene into a silkworm enables expression of the modified bagworm Fib H gene in the posterior silkgland of the silkworm.

(2) Vector Composed of Two Expression Units

In cases where the expression vector of a modified bagworm Fib H gene is composed of two gene expression units of first and second expression units, the essential components for the expression of the modified bagworm Fib H gene are divided into each unit. In this configuration, the expression vector of a modified bagworm Fib H gene is functional only if the first and second expression units coexist in host cells.

In explaining the mechanism specifically, when the first and second expression units coexist in a host cell, a promoter for expression in the posterior silkgland comprised in the first expression unit is activated to drive expression of a transcriptional regulator from the first expression unit in the same cell. The transcriptional regulator binds to and activates a target promoter on the second expression unit, whereby the modified bagworm Fib H gene of interest can be expressed. The first and second expression units have the following configurations.

The "first expression unit" comprises a promoter for expression in the posterior silkgland and a gene of a transcriptional regulator placed under the control of the promoter. Here, two or more identical or different transcriptional regulators may be comprised under the control of one promoter.

The first expression unit may have two or more sets, each of which consists of a promoter for expression in the posterior silkgland and a gene of a transcriptional regulator under the control thereof. In this case, each set may be the same set or a different set. For example, the first expression unit may comprise a set consisting of the Fib H promoter and the GAL4 gene and another set consisting of the Fib L promoter and the GAL4 gene.

Any known promoter for expression in the posterior silkgland and any known transcriptional regulator can be used as the promoter and transcriptional regulator comprised in the first expression unit. Thus, any existing gene expression vector comprising a promoter for expression in the posterior silkgland and a transcriptional regulator can also be reutilized as the first expression unit.

The "second expression unit" comprises a promoter targeted by the transcriptional regulator encoded in the above-described first expression unit and the modified bagworm Fib H gene placed under the control of the target promoter. The target promoter comprised in the second expression unit is a promoter activated by the transcriptional regulator encoded in the first expression unit. In other words, the target promoter comprised in the second expression unit is in principle uniquely determined depending on the transcriptional regulator encoded in the first expression unit. For example, when a gene of a transcriptional regulator comprised in the first expression unit is the GAL4 gene, the promoter targeted by Gal4 in the second expression unit is UAS.

The second expression unit may comprise two or more modified bagworm Fib H genes under the control of one target promoter, each of which may have the same or a different sequence.

Further, the second expression unit may have two or more sets, each of which consists of a target promoter and the modified bagworm Fib H gene under the control of the target promoter. In this case, each set may be the same set or a different set.

Furthermore, the second expression unit may be composed of two or more identical or different units, each of which comprises the modified bagworm Fib H gene. In this case, the transcriptional regulator expressed from a single first expression unit can activate the target promoters in multiple second expression units to allow for the expression of the modified bagworm Fib H gene comprised in each of the second expression units.

In the expression vector of a modified bagworm Fib H gene of this configuration, the expression of the modified bagworm Fib H gene in the second expression unit can be amplified through the transcriptional regulator encoded in the first expression unit. Thus, this configuration is suitable for overexpression of the modified bagworm Fib H gene in host cells.

3. Transgenic Silkworm 3-1. Summary

The third aspect of the present invention is a transgenic silkworm. The transgenic silkworm of this aspect is a transformant comprising the above-described expression vector of a modified bagworm Fib H gene of the second aspect. The silk spun by the transgenic silkworm of the present invention is a modified bagworm silk comprising the modified bagworm Fib H based on silkworm silk. Thus, mass production of the modified bagworm silk is enabled by allowing the transgenic silkworm of the present invention to cocoon.

3-2. Configuration

The transgenic silkworm of the present invention comprises the expression vector of a modified bagworm Fib H gene according to the second aspect described above in its cells. Because the details of the configuration of the expression vector of a modified bagworm Fib H gene have been described in the second aspect, the explanation thereof is omitted and the configuration specific to the transgenic silkworm of this aspect is described here.

In the transgenic silkworm, the expression vector of a modified bagworm Fib H gene according to the second aspect may exist transiently in silkworm cells or may stably continue to exist in a state where it is introduced in the chromosome, and is typically preferred to stably continue to exist.

The transgenic silkworm may have two or more different expression vectors of a modified bagworm Fib H gene according to the second aspect. For example, the transgenic silkworm may comprise the first and second units of the above-described expression vector composed of one gene expression unit and the expression vector composed of two gene expression units. In this case, each expression vector of a modified bagworm Fib H gene may comprise a modified bagworm Fib H gene of the same or a different base sequence.

In cases where the expression vector of a modified bagworm Fib H gene is composed of two expression units of the first and second expression units and each of the expression units is present on a silkworm chromosome, each expression unit may be present on the same or may be present on a different chromosome. In cases where each expression unit is present on a different chromosome, a transgenic silkworm line having the first expression unit alone (preferably in homozygous state) and a transgenic silkworm line having the second expression unit alone (preferably in homozygous state) may be crossed, whereby transgenic silkworms of the present invention having both the first and second expression units can be easily obtained in F1. In this case, any existing transgenic silkworm line having the first expression unit alone may be reutilized because such a transgenic silkworm line having the first expression unit alone as described above is highly versatile.

On the other hand, in cases where the first and second expression units are present on an identical chromosome, the expression units are preferably located closely and linked to each other, not to be separated from one another by recombination across generations.

3-3. Production Method

Any known method can be used as a method of producing the transgenic silkworm of this aspect, which is not particularly limited. Examples of the method of producing the transgenic silkworm include a method of directly introducing the expression vector of a modified bagworm Fib H gene of the second aspect described above into host silkworms, and a method of mating male and female transgenic silkworms each of which has either the first or second expression units of the expression vector of a modified bagworm Fib H gene according to the second aspect on a different chromosome.

(1) Method of Direct Introduction

This method is a method of producing a transgenic silkworm adopted mainly when the expression vector of a modified bagworm Fib H gene of the second aspect is composed of one expression unit. According to this method, the purpose can be achieved by introducing the expression vector of a modified bagworm Fib H gene into host silkworms and then selecting a transgenic silkworm comprising the expression vector. This production method comprises an introduction step and a selection step as essential steps.

(Introduction Step)

The "introduction step" is the step of introducing the expression vector of a modified bagworm Fib H gene according to the second aspect into host silkworms. Any method known in the art may be used as a method of introducing the expression vector into silkworms. For example, the method of Tamura et al (Tamura T. et al., 2000, Nature Biotechnology, 18, 81-84) can be used for introduction into silkworm eggs. Specifically, a dosing solution is prepared by diluting the expression vector of a modified bagworm Fib H gene in a solvent such as water or buffer to obtain an appropriate concentration of the expression vector of a modified bagworm Fib H gene. In cases where the expression vector of a modified bagworm Fib H gene has an inverted terminal repetitive sequence of a transposon, a helper vector comprising DNA encoding a transposase may be added to the dosing solution and co-injected into silkworm eggs at early developmental stages. The host silkworm used for this is not particularly limited, and may be the wild type or a mutant silkworm, or a transgenic silkworm. Further, in cases where a host silkworm already comprises such a helper vector, a dosing solution only comprising the expression vector of a modified bagworm Fib H gene without addition of a helper vector, may be injected into silkworm eggs at early developmental stages.

(Selection Step)

The "selection step" refers to the step of selecting a transgenic silkworm comprising the expression vector of a modified bagworm Fib H gene from silkworms after the introduction step. Any method known in the art is used as the selection method, which is not particularly limited. The transgenic silkworm of interest can typically be obtained by selecting a transformant on the basis of the presence or absence of a selection marker, which is produced by the expression of a marker gene comprised in the expression vector of a modified bagworm Fib H gene (in cases where a helper vector is introduced, the same applies to the helper vector as well).

In a transgenic silkworm obtained by the method using a helper vector, the introduced expression vector of a modified bagworm Fib H gene has been integrated into a chromosome via inverted terminal repetitive sequence of the transposon. Thus, the obtained transgenic silkworm may subsequently be subjected to a step of sib mating or inbreeding, as necessary, to obtain a homozygote for the expression vector inserted into the chromosome.

(2) Method of Mating and Selection

This method is a method of producing a transgenic silkworm mainly adopted when the expression vector of a modified bagworm Fib H gene of the second aspect is composed of two expression units. According to this method, the purpose can be achieved by crossing male and female transgenic silkworms each of which has either the first or second expression unit on a different chromosome, and then selecting a transgenic having the two expression units in F1 or F2. This production method comprises the mating step and the selection step as essential steps.

(Mating Step)

The "mating step" refers to the step of mating a transgenic silkworm having the first expression unit (the first transgenic silkworm) with a transgenic silkworm having the second expression unit (the second transgenic silkworm). The two silkworm lines may be crossed according to a conventional method.

(Selection Step)

The "selection step" is the step of selecting a transgenic silkworm line having the first and second expression units described above. This step can be accomplished by selecting an individual having both the first and second expression units on the basis of the activity of selection markers encoded in each of the first and second expression units from F1 progenies obtained after the mating step or the F2 progenies obtained by mating between the F1 progenies. The first and second transgenic silkworms can be generated by introducing either the first or second expression unit into silkworms using the direct introduction method described above.

4. Method of Producing Modified Bagworm Silks

4-1. Summary

The fourth aspect of the present invention is a method of producing a modified bagworm silk. The production method of the present invention uses a transgenic silkworm for mass protein production. The transgenic silkworm used in this aspect is the transgenic silkworm of the third aspect. Modified bagworm silks are obtained from cocoons produced by the silkworms. By the production method of the present invention, mass production of a hybrid silk between bagworm silk and silkworm silk having the physical properties of bagworm silk, namely a modified bagworm silk, can be performed using, for example, production facilities for silkworm silks.

4-2. Method

The method of producing modified bagworm silk of the present invention comprises the rearing step as an optional step and also comprises the cocooning step, cocoon collecting step, and reeling step as essential steps.

(1) Rearing Step

The "rearing step" is a step of rearing the transgenic silkworm of the third aspect. The transgenic silkworm may be reared according to any silkworm rearing technique known in the art. See, for example, Takeo Takami, "Silkworm Eggs: An Overview," ZENKOKU SANSHU KYOUKAI. Natural leaves of species of food grasses and trees, such as leaves of the genus *Morus*, or an artificial diet, such as SilkMate L4M or SilkMate for 1-3 instar larvae of original race (Nosan Corporation), may be used as a diet. An artificial diet is preferred because it is possible to prevent disease development, to provide a stable quality and quantity of a diet, and also to rear silkworms under a sterile condition as necessary. A simple method of rearing the transgenic silkworm will be described by way of an example below.

Beginning of silkworm rearing is performed with eggs laid by an appropriate number (for example, 4 to 10) of female transgenic silkworms of the same line. The hatched larvae are transferred from a silkworm egg paper to dry-proof paper (paraffin-coated paper) as a rearing bed spread out in a container and fed with an artificial diet such as the SilkMate, which is placed on the dry-proof paper. In principle, the diet is exchanged once each in the first and second instars and once to three times in the third instar. If there is a large amount of leftover, old food is removed to prevent decay. For rearing the 4th to 5th instar grown silkworm larvae, the larvae are transferred to a large container and the number of larvae per one container is appropriately adjusted. The container may be covered with dry-proof paper, an acrylic lid, or a mesh lid, depending on the humidity or the internal state of the container. The rearing temperature is kept from 25 to 28° C. throughout all the instars.

(2) Cocooning Step

The "cocooning step" is the step of allowing the transgenic silkworm of the third aspect to cocoon. The term "cocoon(ing)" refers to the formation of a cocoon for pupation by a silkworm at the final (fifth) instar.

This step may be performed basically according to any cocooning method known in the silkworm. For example, this step can be accomplished by collecting matured silkworm at the sixth to eighth day in the final instar and mounting them. The term "mounting" refers to transferring silkworms onto a cocooning frame. The cocooning may be performed at a temperature of 25 to 28° C. Subsequently, the transgenic silkworms of the third aspect form cocoons in the cocooning frame.

(3) Cocoon Collecting Step

The "cocoon collecting step" refers to the step in which, following the cocooning step, cocoons are separated off from a cocooning frame and collected. This step also comprises removing the floss attached around the cocoons. Cocoon collection may be performed six to eight days after mounting. Cocoon colloection may be performed manually, but is conveniently performed using a cocoon harvester. In addition to remover of cocoon floss which only removes floss, automatic cocoon harvester attached with floss remover can be used, which carry out separation of cocoons from a cocooning frame and up to removal of floss.

(4) Reeling Step

The "reeling step" refers to the step of reeling the modified bagworm silk from cocoons collected in the cocoon collecting step. The term "reeling" refers to producing raw silk from cocoons. The collected cocoon is subjected to "cocoon cooking" in which the cocoon is immersed in hot water at a temperature of 80 to 85° C. to unwind the cocoon, to "brushing" in which the surface of the cocoon is brushed with a brush for brushing, then to "picking end" in which end of thread is picked up from the cocoon, and to reeling. These steps can be performed manually, but are preferably performed using an automatic reeling machine, which is a specilized machine for reeling. By the steps described above, the modified bagworm silk can be produced as a raw silk.

EXAMPLES

Example 1

Cloning of the Bagworm Fib H Gene (Object)

The object is to clone an unknown bagworm Fib H gene.

(Method)

Larvae of *Eumeta japonica* collected outdoors in Abiko, Chiba, Japan were dissected to isolate silkglands. The isolated silkglands were homogenized in RNA extraction reagent, ISOGEN (Nippon Gene Co. Ltd.) and total RNA was extracted using SV Total RNA Isolation system (Promega Corporation). The extracted total RNA was used as a template to produce a cDNA library using TruSeq RNA Sample Preparation Kit v2 (Illumina Inc.). The resulting cDNA library was subjected to RNAseq analysis using a next-generation sequencer Hiseq 2500. The obtained 101bp×2 paired-end read sequence data was used for de novo assembly analysis using blast search and trinity.

(Results)

The de novo assembly analysis successfully identified an about 750-bp base sequence shown in SEQ ID NO: 24 encoding the N-terminal region of the *Eumeta japonica* Fib H, an about 1020-bp base sequence shown in SEQ ID NO: 25 encoding the repetitive sequence in the central region of the *Eumeta japonica* Fib H, and an about 300-bp base sequence shown in SEQ ID NO: 26 encoding the C-terminal region of the *Eumeta japonica* Fib H.

Example 2

Construction of an Expression Vector of a Modified Bagworm Fib H (Object)

The object is to construct an expression vector of a full-length chimeric Fib H gene on the basis of the information of the partial sequences of the bagworm Fib H gene from *Eumeta japonica* obtained in Example 1 and the information of the silkworm Fib H gene.

(Method and Results)

The information of the base sequences obtained in Example 1 corresponded to partial regions in the bagworm Fib H gene from *Eumeta japonica* (N-terminal, central, and C-terminal regions). The transcription product of the *Eumeta japonica* Fib H gene is predicted to have a total length of about 10 kbp. Thus, to make a recombinant construct in a form that can be used from the bagworm Fib H gene, a modified bagworm Fib H gene consisting of a chimeric gene between the bagworm and silkworm was constructed by the following procedures, based on the information of the base sequences of the fragments of *Eumeta japonica* Fib H gene obtained in Example 1 and the information of the silkworm Fib H gene.

The modified bagworm Fib H gene of this Example has been constructed without using the information of the base sequences of the N-terminal and C-terminal regions obtained in Example 1 because use of the N-terminal and C-terminal regions of the silkworm Fib H gene was considered to be preferable to allow the modified bagworm Fib H gene to be expressed appropriately in the posterior silkgland of silkworm and the resulting protein to be secreted without any abnormalities as a modified bagworm silk. In addition, since the physical properties specific to each silk are generally attributed to the region consisting of the repetitive sequences, use of only the central region encoding the repetitive sequence from the bagworm was considered to be sufficient to impart the physical properties of bagworm silk to silkworm silk.

Two sets of primer pairs were designed such that gene regions encoding the N-terminal region and the repetitive sequence portion, and the repeat portion and the C-terminal region of the gene were respectively amplified. Individual PCRs were performed using the two sets of primer pairs, i.e., the 5' side primer pair shown in SEQ ID NOs: 27 and 28 (EvHFB-F21 and -R26, respectively) and the 3' side primer pair shown in SEQ ID NOs: 29 and 30 (EvHFB-F26 and -R12, respectively). Subsequently, 1/50 volumes of the reaction mixtures containing the amplification products (Ev01HFB-F21/R26 and Ev01HFB-F26/R12) after the respective PCRs were diluted 1000 times to produce a template solution. The solution was used for PCR with the N-terminal primer (EvHFB-F12) shown in SEQ ID NO: 31 and the C-terminal primer (EvHFB-R12) shown in SEQ ID NO: 30 and the resulting amplified fragment (Ev01HFB-F12/R12) was collected. Then, only repeat portion of this amplified fragment was PCR amplified with a forward primer (EvHFB-F31) shown in SEQ ID NO: 32 and a reverse primer (EvHFB-R31) shown in SEQ ID NO: 33 to obtain an amplified fragment (Ev01HFB-F31/R31). The amplified fragment was cloned into T-vector pCR4TOPO (Thermo Fisher Scientific Inc.) and then excised by BglII and SalI On the other hand, the silkworm green fluorescent Fib H construct "pHChis6-EGFP" (Kuwana Y., et al., 2014, PLoS ONE 9(8):e105325) was digested with BglII and SalI such that the vector backbone and the N-terminal and C-terminal sequences of silkworm Fib H remained. The ligation solution of the two fragments was used for transformation, and the modified bagworm Fib H, "pHC.BmEv01HFB-F31/R31s" was produced. A fragment obtained by AscI and FseI cleavage of the "pHC.BmEv01HFB-F31/R31.03" clone selected from it, and a fragment obtained by AscI and FseI cleavage of the piggyBac vector "pBac3xP3eGFP" were ligated, and tranformation with the ligation solution established an expression vector of a modified bagworm Fib H gene (pBac3xP3eGFP-BmEv01HFB-F31/R31) as a hybrid gene that can be expressed in the silkgland of silkworm.

Example 3

Establishment of Transgenic Silkworms (Object)
The object is to produce a transgenic silkworm introduced with the expression vector established in Example 2.
(Method and Results)
The expression vector of a modified bagworm Fib H gene (pBac3xP3eGFP-BmEv01HFB-F31/R31) established in Example 2 was injected into 288 eggs of the silkworm wlpnd strain according to a conventional method (Tamura T. et al., 2000, Nat Biotechnol, 18: 81-84), and the resulting adult insects were sib-mated (G0 mating) to produce 38 moth groups. Among these groups, recombinants of 92 individuals (G1 eggs) from eight moth groups were subjected to screening. Fifty-six individuals hatched from G1 eggs, and 34 individual adult insects of the modified bagworm Fib H gene transgenic silkworms were obtained.

Production of modified bagworm Fib H gene transgenic silkworms was performed again by a similar method. pBac3xP3eGFP-BmEv01HFB-F31/R31 was injected into 384 eggs of the silkworm wlpnd strain according to the above-described conventional method. After rearing 120 hatched individuals, the resulting G0 adult insects were sib-mated to obtain G1 eggs in 38 moth groups. After incubating eggs, screening was performed based on the GFP marker in eye of the embryo and GFP-positive individuals were consequently obtained in eight moth groups. The GFP-positive individuals are transgenic silkworms capable of expressing the modified bagworm Fib H gene of interest. The individual moth groups were named Y91.01 to Y91.08 in descending order according to the number of positive individuals. Transgenic silkworms in the top three (Y91.01 to Y91.03) among these moth groups were used in the following experiments. GFP-negative individuals obtained in this step were used as control individuals (Y90.Cont.) which do not have the expression vector of a modified bagworm Fib H gene. G1 individuals in the above-described three moth groups and the control G1 individuals were each sib-mated to obtain G2 eggs, and thereafter the G2 individuals were cultivated and again sib-mated to obtain G3 eggs. Cocoons obtained from the larvae in this G3 generation were subjected to reeling using an automatic reeling machine for quality control of cocoons (NISSAN MOTOR CO., LTD., Type CT-2) with a target fineness of 27 d and at a reeling speed of 200 m/min. After leaving the obtained silk at a target temperature and humidity set at 20° C. and 65% for two hours or more, the physical properties (breaking strength, breaking elongation, and Young's modulus) of the silk were measured at a sample length of 100 mm and a pulling speed of 150 mm/min. The breaking strength refers to the stress applied immediately before breaking. In general, a larger value thereof means that the subject material can endure a stronger stress. The breaking elongation refers to the elongation resulting in breaking. In general, a larger value thereof means that the subject material elongates better. The Young's modulus is the constant of proportionality between stress and strain in the same axial direction in the range of elasticity in which Hooke's law holds. In general, a larger value thereof means that the stiffness of the subject material is higher.

The result is shown in Table 1.

TABLE 1

| | Strain | Breaking strength (g/d) | Breaking elongation (%) | Young's modulus (kg/mm$^2$) |
|---|---|---|---|---|
| Recombinant silkworm silk | Y91.01 | 5.04 | 23.2 | 1.498 |
| | Y91.02 | 4.91 | 23.8 | 1.518 |
| | Y91.03 | 4.81 | 23.4 | 1.497 |
| Control silk | Y91.Cont. | 4.79 | 14.4 | 1.204 |

The recombinant silkworm silk is a silk spun by the modified bagworm Fib H transgenic silkworms, and corresponds to a hybrid silk between the modified bagworm silk and silkworm silk derived from the wlpnd strain. Further, the control silk corresponds to a silkworm silk derived from the wlpnd strain.

Table 1 indicates that elongation and Young's modulus of the recombinant silkworm silk derived from any strains of the transgenic silkworm are remarkably increased as compared to those of the control silk, suggesting that the modified bagworm silk provided elasticity and stiffness to the silkworm silk.

All publications, patents, and patent applications cited herein are incorporated herein by reference in their entirety.

The invention claimed is:

1. A gene encoding a modified bagworm fibroin H chain, wherein the modified bagworm fibroin H chain is a chimeric fibroin H chain comprising a bagworm fibroin H chain fused to a portion of a silkworm fibroin H chain, wherein the modified bagworm fibroin H chain comprises (a) or (b):

(a) an amino acid sequence comprising positions 1 to 153 of SEQ ID NO: 9,
one or a plurality of the amino acid sequences set forth in SEQ ID NOs: 5 and/or 7, and
an amino acid sequence comprising positions 466 to 524 of SEQ ID NO: 9, (b) an amino acid sequence comprising positions 1 to 153 of SEQ ID NO: 9,
one or a plurality of an amino acid sequence having an amino acid identity of 90% or more to full length SEQ ID NOs: 5 and/or 7, and
an amino acid sequence comprising positions 466 to 524 of SEQ ID NO: 9.

2. An expression vector of a modified bagworm fibroin H chain gene, the vector comprising a promoter for expression in the posterior silk gland derived from a silk spinning insect, and the modified bagworm fibroin H chain gene according to claim 1, wherein the promoter is operably linked to said gene.

3. The expression vector of a modified bagworm fibroin H chain gene according to claim 2,
wherein the expression vector comprises:
a first expression unit comprising a promoter for expression in the posterior silk gland derived from a silk spinning insect operably linked to a gene encoding a transcriptional regulator; and
a second expression unit comprising a promoter operably linked to the modified bagworm fibroin H chain gene, wherein the promoter operably linked to the modified bagworm fibroin H chain gene is targeted by the transcriptional regulator.

4. The expression vector of a modified bagworm fibroin H chain gene according to claim 3, wherein the gene encoding the transcriptional regulator is a GAL4 gene and the promoter targeted by the transcriptional regulator is a UAS promoter.

5. The expression vector of a modified bagworm fibroin H chain gene according to claim 2, wherein the promoter for expression in the posterior silkgland is a posterior silk gland-specific promoter.

6. The expression vector of a modified bagworm fibroin H chain gene according to claim 5, wherein the posterior silk gland-specific promoter is a promoter of any of fibroin H chain, fibroin L chain, or p25.

7. The expression vector of a modified bagworm fibroin H chain gene according to claim 2, wherein the silk spinning insect is a silkworm.

8. A transgenic silkworm comprising the expression vector of a modified bagworm fibroin H chain gene according to claim 2, wherein the transgenic silkworm expresses the modified bagworm fibroin H chain.

9. A method of producing a transgenic silkworm that spins a modified bagworm silk, comprising:
   introducing the expression vector of a modified bagworm fibroin H chain gene according to claim 6 into a host silkworm; and
   selecting a transgenic silkworm comprising the expression vector, wherein the transgenic silkworm expresses the modified bagworm fibroin H chain.

10. A method of producing a transgenic silkworm that spins a modified bagworm silk, comprising:
   crossing a transgenic silkworm having a first expression unit comprising a promoter for expression in the posterior silk gland derived from a silk spinning insect and a gene encoding a transcriptional regulator placed under the downstream control of the promoter and a transgenic silkworm having a second expression unit comprising a promoter targeted by the transcriptional regulator and the modified bagworm fibroin H chain gene placed under the downstream control of the targeted promoter; and
   selecting a transgenic silkworm having the first and second expression units from progenies after the cross.

* * * * *